(12) United States Patent
Pelletier et al.

(10) Patent No.: US 7,425,573 B2
(45) Date of Patent: Sep. 16, 2008

(54) USE OF ANNELLATED PYRROLE COMPOUNDS IN THE TREATMENT OF ARTICULAR CARTILAGE OR SUBCHONDRAL BONE DEGENERATION

(75) Inventors: Jean-Pierre Pelletier, St. Lambert (CA); Johanne Martel-Pelletier, St. Lambert (CA)

(73) Assignees: Merckle GmbH, Blaubeuren (DE); Ascentia Pharma Inc., Montreal (CA)

( * ) Notice: Subject to any disclaimer, the term of this patent is extended or adjusted under 35 U.S.C. 154(b) by 263 days.

(21) Appl. No.: 10/486,912

(22) PCT Filed: Aug. 29, 2002

(86) PCT No.: PCT/EP02/09658

§ 371 (c)(1),
(2), (4) Date: Jul. 21, 2004

(87) PCT Pub. No.: WO03/020267

PCT Pub. Date: Mar. 13, 2003

(65) Prior Publication Data

US 2005/0004108 A1 Jan. 6, 2005

Related U.S. Application Data

(60) Provisional application No. 60/315,773, filed on Aug. 30, 2001.

(30) Foreign Application Priority Data

Aug. 30, 2001 (CA) .................................. 2356099

(51) Int. Cl.
*A61K 31/40* (2006.01)
*A61K 31/70* (2006.01)
*A61K 31/65* (2006.01)

(52) U.S. Cl. .................... 514/413; 514/23; 514/62; 514/154

(58) Field of Classification Search ............... None
See application file for complete search history.

(56) References Cited

U.S. PATENT DOCUMENTS

| 4,232,038 A |   | 11/1980 | Kluge et al. |
| 4,704,356 A | * | 11/1987 | Thonar ...................... 435/7.92 |
| 5,095,037 A | * | 3/1992 | Iwamitsu et al. ............ 514/561 |
| 5,260,451 A |   | 11/1993 | Dannhardt et al. |
| 5,310,759 A | * | 5/1994 | Bockman .................... 514/573 |
| 5,464,609 A |   | 11/1995 | Kelm et al. |
| 2004/0122002 A1 |   | 6/2004 | Striegel et al. |

FOREIGN PATENT DOCUMENTS

| DE | 196 24 289 | 1/1998 |
| DE | 196 24 290 | 1/1998 |
| DE | 198 45 446 | 4/2000 |
| DE | 100 01 166 | 7/2001 |
| DE | 100 04 157 | 8/2001 |
| WO | 95 32971 | 12/1995 |
| WO | 95 32972 | 12/1995 |
| WO | 01 05792 | 1/2001 |

OTHER PUBLICATIONS

Rabasseda et al., "2-[6-(4-Chlorophenyl)-2,2-dimethyl-7-phenyl-2,3-dihydro-1H-pyrrolizin-5-yl)acetic acid", Drugs of the Future, vol. 20, No. 10, pp. 1007-1009.*
Abramson SB et al., "Prospects for disease modification in osteoarthritis", Nat. Clin. Pract. Rheumatol., Jun. 2006; 2(6):304-12, (Abstract only).*
Laufer, S. et al. "Acute and Chronic Anti-inflammatory Properites of [2,2-Dimethyl-6-(4-chlorophenyl)-7-phenyl-2,3-dihydro-1H-pyrrolizine-5-yl]-acetic Acid", Arzneimittel-Forschung, vol. 45, No. 1, pp. 27-32, XP001109132; ISSN: 0004-4172 1995.
Tries, S. et al. "ML3000, A Novel Anti-Inflammatory Compound without the Potential for Causing Gastric Damage", Inflammation Research, vol. 50, No. Supplement 3, p. S203, XP008010188, ISSN: 1023-3830 2001.
Tries, S. et al. "Pharmacological Profile of ML3000: A new gastric mucosa sparing anti-inflammatory drug with COX/5-LOX Inhibitory Activity", Inflammation Research, vol. 50, No. Supplement 3, p. S187, XP008010187, ISSN: 1023-3830 2001.
Gay, Renate E. et al. "Dual Inhibition of 5-Lipoxygenase and Cyclooxygenases 1 and 2 by ML3000 Reduces Joint Destruction in Adjuvant Arthritis", Journal of Rheumatology, vol. 28, No. 9, pp. 2060-2065, XP008008719, ISSN: 0315-162X 2001.

(Continued)

*Primary Examiner*—Raymond J. Henley, III
(74) *Attorney, Agent, or Firm*—Oblon, Spivak, McClelland, Maier & Neustadt, P.C.

(57) ABSTRACT

Treating or preventing degeneration or destruction of articular cartilage and/or subchondral bone in the affected joint of a mammal is accomplished by administering a compound of formula (I), wherein the variables have the meanings given in the present description. A preferred compound of formula (I) is formula (II). This treatment ameliorates, diminishes, actively treats, reverses or prevents any injury, damage or loss of articular cartilage or subchondral bone subsequent to said early stage of said degeneration

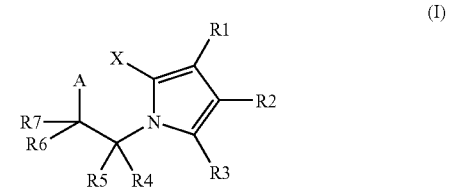
(I)

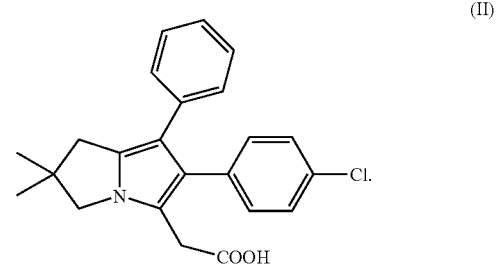

(II)

19 Claims, 10 Drawing Sheets

OTHER PUBLICATIONS

Laufer, Stefan. "Discovery and Development of ML3000", Inflammopharmacology, vol. 9, No. 1.2, pp. 101-112, XP008008718, ISSN: 0925-4692 2001.

Dannhardt, Gerd et al. "Aminomethylierung und Arylthiolierung von 6.7-Diaryl-2.3-dihydro-1H-pyrrolizinen", Arch. Pharm. vol. 319, pp. 65-69 (with English abstract). 1986.

Dannhardt, Gerd et al. "Oxidative Ringoeffnung von 6.7-Diphenyl-2.3-dihydro-1H-pyrrolizin (DADHP) durch m-Chlorperbenzoesaeure", Arch. Pharm. vol. 319, pp. 231-234 (with English abstract). 1986.

Dannhardt, Gerd et al. "Natriummetaperiodat-Oxidation von 6.7-Diphenyl-2.3-dihydro-1H-pyrrolizin", Arch. Pharm. vol. 318, pp. 661-663 1985.

Dannhardt, Gerd et al. "6.7-Diaryl-2.3-dihydro-1H-pyrrolizine (DADHP) als Singulett-Sauerstoff-Faenger", Arch. Pharm. vol. 318, pp. 663-664 1985.

Dannhardt, Gerd et al. "Synthese und Oxidation von 6.7-Diphenyl-2.3-dihydro-1H-pyrrolizin-5-yl-acetaldehyd (DADHP-5-acetaldehyd)", Arch. Pharm., vol. 319, pp. 500-505 (with English abstract). 1986.

Dannhardt, Gerd et al. "6.7-Diarylsubstituierte 1- und 3-Pyrrolizinone (1-DAPON und 3-DAPON)", Arch. Pharm. vol. 319, pp. 749-755 (with English abstract). 1986.

Dannhardt, G. et al. "C-5 Functionalized 6,7-Diphenyl-2,3-dihydro-1H-pyrrolizines as Inhibitors of Bovine Cyclooxygenase and 5-Lipoxygenase", Arch. Pharm. vol. 327, pp. 509-514 1994.

Laufer, Stefan et al. "Synthesis and Evaluation of a Novel Series of Pyrrolizine Derivatives as Dual Cyclooxygenase-1 and 5-Lipoxygenase Inhibitors", Arch. Pharm. vol. 330, pp. 307-312 1997.

Muchowski, Joseph M. et al. "Synthesis and Antiinflammatory and Analgesic Activity of 5-Aroyl-1,2-dihydro-3H-pyrrolo[1,2-a]pyrrole-1-carboxylic Acids. The 6-substituted compounds", J. Med. Chem. vol. 30, pp. 820-823 1987.

Laufer, Stefan A. et al. "(6,7-Diaryldihydropyrrolizin-5-yl)acetic Acids, a Novel Class of Potent Dual Inhibitors of Both Cyclooxygenase and 5-Lipoxygenase", J. Med. Chem. vol. 37, pp. 1894-1897 1994.

Rabasseda, X. et al. "2-[6-(4-Chlorophenyl)-2,2-dimethyl-7-phenyl-2,3-dihydro-1H-pyrrolizin-5-yl]acetic acid", Drugs of the Future, vol. 20, No. 10, pp. 1007-1009 1995.

Fernandes, Julio C. et al. "Effects of Tenidap on Canine Experimental Osteoarthritis", Arthritis & Rheumatism, vol. 38, No. 9, pp. 1290-1303 1995.

Pelletier, Jean-Pierre et al. "Carprofen Simultaneously Reduces Progression of Morphological Changes in Cartilage and Subchondral Bone in Experimental Dog Osteoarthritis", The Journal of Rheumatology, vol. 27, No. 12, pp. 2893-2902 2000.

S. Laufer, et al., "Pharmacological Profile of a New Pyrrolizine Derivative Inhibiting the Enzymes Cyclo-oxygenase and 5-Lipoxygenase", Arzneim-Forsch./Drug Res., vol. 44, No. 1, 1994, 629-636.

Jean-Pierre Pelletier, et al., "Selective Inhibition of Inducible Nitric Oxide Synthase in Experimental Osteoarthritis Is Associated with Reduction in Tissue Levels of Catabolic Factors", The Journal of Rheumatology, 1999, pp. 2002-2012, 2014 (p. 2013 will be filed later).

Julio C. Fernandez, et al., "The Effects of Tenidap on Canine Experimental Osteoarthritis: II. Study of the Expression of Collagenase-1 and Interleukin 1β by in Situ Hybridization", The Journal of Rheumatology, 1998, pp. 951-958.

Jean-Pierre Pelletier, et al., "In Vivo Protective Effects of Prophylactic Treatment with Tiaprofenic Acid or Intraarticular Corticosteroids on Osteoarthritic Lesions in the Experimental Dog Model", Journal of Rheumatology, (Suplemental 27) vol. 18, 1991, pp. 127-130.

Marshall J. Palmoski, et al., "In Vivo Effects of Aspirin on Canine Osteoarthritic Cartilage", Arthritis and Rheumatism, vol. 26, No. 8, Aug. 1983, pp. 994-1001.

Henry J. Mankin M.D. et al., "Biochemical and Metabolic Abnormalities in Articular Cartilage from Osteo-Arthritic Human Hips", The Journal of Bone and Joint Surgery, vol. 53-A, No. 3, Apr. 1971, pp. 523-537.

Jean-Pierre Pelletier, et al., "Role of Synovial Membrane Inflammation in Cartilage Matrix Breakdown in the Pond-Nukl Dog Model of Osteoarthritis", Arthritis and Rheumatism, vol. 28, No. 5, May 1985, pp. 554-561.

Florina Moldovan, et al., "Collagenase-3 (Matrix Metalloprotease 13) Is Preferentially Localized in the Deep Layer of Human Arthritic Cartilage in Situ", Arthritis and Rheumatism, vol. 40, No. 9, Sep. 1997, pp. 1653-1661.

Edward C. Huskisson, et al., "Effects of Antiinflammatory Drugs on the Progression of Osteoarthritis of the Knee", The Journal of Rheumatology, pp. 1941-1946, (1995).

Daniel Lajeunesse, et al., Demonstration of an Osteoblast Defect in Two Cases of Human Malignant Osteopetrosis, J. Clin. Invest., The American Society for Clinical Investigation, Inc. vol. 98, No. 8, Oct. 1996, 1835-1842.

Jean-Pierre, et al. "Etiopathogenesis of Osteoarthritis" Arthritis and Allied Conditions: a textbook of rheumatoglogy, 2001, 14th ed., pp. 22195-2215.

J. Martel-Pelletier, et al., "Biochemical Factors in Joint Articular Tissue Degradation in Osteoarthritis", Osteoarthritis: clinical and experimental aspects, 199, pp. 156-187.

Jean-Pierre Pelletier, et al., "Intraarticular injections with Methylprednisolone Acetate Reduce Osteoarthritic Lesions in Parallel With Chondrocyte Stromelysin Synthesis in Experimental osteoarthritis", Arthritis Rheum, Mar. 1994, 37(3) pp. 414-423.

* cited by examiner

Fig. 1

| Group | No. of Animals | Femoral condyles | | Tibial plateaus | |
|---|---|---|---|---|---|
| | | Size (mm²) | Grade (0-4 scale) | Size (mm²) | Grade (0-4 scale) |
| OA | 7 | 23.4 ± 6.6 | 1.96 ± 0.3 | 45.5 ± 5.9 | 2.25 ± 0.3 |
| ML3000 (2.5 mg/kg/day) | 7 | 14.3 ± 6.9 (P < 0.05) | 1.21 ± 0.4 | 25.1 ± 6.9 (P < 0.01) | 0.93 ± 0.2 (P < 0.004) |
| ML3000 (5 mg/kg/day) | 7 | 8.5 ± 3.2 (P < 0.04) | 1.07 ± 0.3 | 21.0 ± 5.8 (P < 0.01) | 1.18 ± 0.4 (P < 0.02) |

Fig. 2

| Group | No. of Animals | Synovial lining (0-2 Scale) | Villous hyperplasia (0-3 Scale) (P) | Cellular Infiltration (0-5 Scale) | Total (0-10) |
|---|---|---|---|---|---|
| OA | 7 | 1.43 ± 0.30 | 2.36 ± 0.24 | 2.36 ± 0.26 | 6.14 ± 0.65 |
| ML3000 (2.5 mg/kg/day) | 7 | 1.43 ± 0.20 | 1.57 ± 0.20 | 1.86 ± 0.56 | 4.86 ± 0.54 |
| ML3000 (5 mg/kg/day) | 7 | 1.00 ± 0.22 | 1.57 ± 0.17 (P<0.04) | 2.43 ± 0.60 | 5.00 ± 0.87 |

| Group | No. of Animals | % of Collagenase-1 positive cells | | % of IL-1ß positive cells |
|---|---|---|---|---|
| | | Femoral condyles (P)* | Tibial plateaus (P) | Synovial Membrane (P) |
| OA | 7 | 29.7 ± 2.5 | 29.6 ± 3.3 | 50.3 ± 2.7 |
| ML3000 (2.5 mg/kg/day) | 7 | 13.4 ± 2.7 (P < 0.0003) | 13.5 ± 2.4 (P < 0.0001) | 32.7 ± 8.6 |
| ML3000 (5 mg/kg/day) | 7 | 7.89 ± 2.2 (P < 0.0004) | 9.54 ± 2.4 (P < 0.0001) | 13.4 ± 2.5 (P < 0.001) |

Fig. 3

USE OF ANNELLATED PYRROLE COMPOUNDS IN THE TREATMENT OF ARTICULAR CARTILAGE OR SUBCHONDRAL BONE DEGENERATION

The present invention relates to the use of annellated pyrrole compounds and in particular of ML3000, salts or derivatives thereof, in mammals as a means of treating and preventing cartilage and/or subchondral bone injury and loss in the inflamed joints of such mammals. Such damage to the cartilage and/or subchondral bone is a natural sequelae of the process of osteoarthritis and its aftermath when it occurs in the mammal. The ability to achieve this unexpected effect is referred to as "chondroprotection".

BACKGROUND OF THE INVENTION

Nonsteroidal antiphlogistika (NSAIDs), such as acetylsalicylic acid (ASA), diclofenac, indomethacin, ibuprofen and naproxen, are widely used in the clinic. From a pharmacological point of view they act as inhibitors of the cyclooxygenase (COX).

Pyrrolizines which pharmacologically act similar, are known from numerous publications. For instance, antiphlogistically active pyrrolizines are described in Arch. Pharm. 319, 65-69 (1986); 319, 231-234 (1986); 318, 661-663 (1985); 318, 663-664 (1985); 319, 500-505 (1986); 319, 749-755 (1986); 327, 509-514 (1994); 330, 307-312 (1997) as well as in J. Med. Chem. 1987, 30, 820-823 and 1994, 37, 1894-1897.

Further pyrrolizines can be taken from U.S. Pat. No. 5,260, 451 (corresponding to EP 0397175) as well as from WO 95/32970; WO 95/32971; and WO 95/32972. These compounds are represented by the structural formula

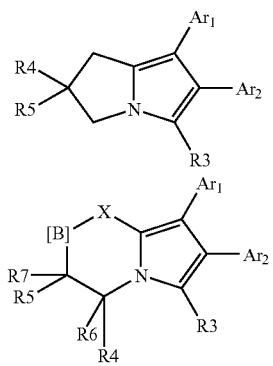

and share an annellated diarylpyrrol moiety as well as a third acidic residue R3. The compounds are characterized by a high lipophilicity, good bioavailability and half-lifes in the medium range, s. Drugs of the Future, 1995, 20 (10):1007-1009.

Further pyrrolizines of similar constitution are described in DE 198 45 446.6 and WO 01/05792. Moreover, alkylsulfinylbenzoyl and alkylsulfonylbenzoyl substituted pyrrolizines, according to U.S. Pat. No. 4,232,038, are said to have anti-inflammatory, analgetic and antipyretic properties. According to DE 196 24 290.8 and DE 196 24 289.4 certain compounds of this type have a lipid-reducing action.

ML3000 ([2,2-dimethyl-6-(4-chlorophenyl)-7-phenyl-2,3-dihydro-1H-pyrrolizine-5yl]-acetic acid) of the Formula (Ia)

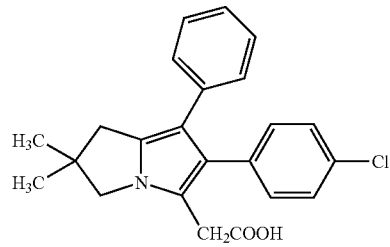

is a non-antioxidant balanced dual inhibitor of COX and 5-Lipoxygenases (5-LO) (3). The drug is a nonselective inhibitor of COX, inhibiting both COX-1 and COX-2. This drug has analgetic, antipyretic and anti-inflammatory activity, and has been demonstrated to have potent anti-inflammatory action in a number of animal models including carrageenan-induced paw edema in the rat, and rat adjuvant arthritis (4).

Osteoarthritis (OA) is the most common of musculoscaletal diseases. It mainly affects the weight-bearing diarthrodial joints such as the hip and knee, but also affects other joints such as interphalangual joints and the spine. The structural changes of this disease include the progressive erosion of the articular cartilage, the formation of osteophytes and, at the clinical stage of the disease, a variable degree of synovial inflammation. Also associated with these changes is a significant remodeling of the subchondral bone, which, according to several studies, is believed to be predominantly an excessive bone resorption in the early stage of the disease, followed by excessive bone formation leading to bone sclerosis and an increased thickening of the subchondral bone.

The mechanisms leading to the development and progression of structural changes seen in osteoarthritis (OA) are multiple and complex, and remain largely unknown. They involve not only cartilage, where a number of morphological changes are observed, but also the synovial membrane which is the site of an inflammatory reaction of variable degree and severity (1). There are a number of pathways believed to be responsible for the catabolism of cartilage matrix including the upregulation of soluble factors, e.g., interleukin-1 (IL-1), tumor necrosis factor-α (TNF-α), and prostaglandins, which can induce loss of articular cartilage. Direct injury to chondrocytes also stimulates matrix metalloprotease (MMP) activity, e.g., collagenases, stromelysins and gelatinases, and the production of various inflammatory mediators (2).

It has to be considered that metabolic processes continuously occur in any given joint that are necessary for its repair and normalization subsequent to it being subjected to an insult such as a traumatic injury.

Accordingly, in order for a compound to be an acceptable chondroprotective agent it must first of all be capable of sustaining such chondrocyte metabolic activity, i.e., of not inhibiting or interfering with the cellular replication and biosynthesis of matrix components which are part of the healing process. In this regard, the skilled artisan will recognize that many NSAIDs display a marked inhibitory action on the biosynthesis of the principal components of the extracellular matrix.

At the same time an acceptable chondroprotective agent must be capable of counteracting the degradative action of mediators such as various cytokines, prostaglandins and proteinases on the cartilage. Accordingly, it has been accepted in the art that potential chondroprotective drugs should be evaluated both as to their positive effects on anabolic pathways as well as to their ability to inhibit catabolic processes. Catabolic events which have typically been monitored include, inter alia, the release and inhibition of matrix degrading enzymes, effects on prostaglandin and leukotriene biosynthesis, and the ability of the drug to inhibit IL-1 mediated degradation of articular cartilage.

A number of drugs like NSAIDs, with activity directed at inhibiting COX enzymes, have been in use for many years. Although they may effectively reduce the symptoms of the osteoarthritis such as pain, they have shown limited ability in reducing the in vivo progression of experimental OA (8,9). While treatment with Tenidap and Carprofen, two NSAIDs with both cyclooxygenase-1 (COX-1) and COX-2 inhibitory activity, were shown to exhibit anti-OA effects (8,9) other NSAIDs, such as diclofenac or ASA, were ineffective (10) or even demonstrated to accelerate cartilage damage in the experimental dog model of OA (11). Similarly, in humans, a recent study in knee OA patients has demonstrated that, based on X-ray criteria, treatment with tiaprofenic acid, a further NSAID, over a 5-year period could not retard the progression of cartilage damage and that indomethacin even accelerated its progression (15).

Surprisingly, it has been found that certain annellated pyrrole compounds, such as ML3000, significantly reduce the development of lesions in experimental dog OA. The protective effect of these compounds was particularly evident in the reduction in the development of cartilage lesions. This phenomenon was associated not only with a significant inhibition of both $PGE_2$ and $LTB_4$ production, but also with an in situ reduction in two major catabolic factors involved in cartilage degradation, namely IL-1β and collagenase-1.

SUMMARY OF THE INVENTION

Thus, the present invention relates to the use of annellated pyrrole compounds represented by the general formula (I):

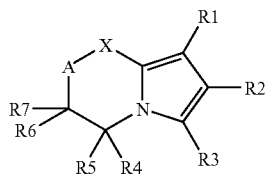

wherein
X represents
  CR8R9, S, O, NR12 or C(O);
A represents
  CR10R11 or a bond between X and the atom carrying radicals R6 and R7;
the first of radicals R1, R2, R3 represents
  aryl, optionally substituted with one or more than one substituents independently selected among the group consisting of halogen, alkyl, halogenoalkyl, alkoxy, aryloxy, halogenoalkoxy, alkylthio, hydroxy, nitro, alkylsulfinyl, alkylsulfonyl, sulfamoyl, N-alkylsulfamoyl, N,N-di-alkylsulfamoyl, alkylsulfonamido and alkylsulfon-N-alkylamido; or
  an aromatic or non-aromatic, mono- or bicyclic, optionally benzoannellated, heterocyclic group having 1, 2 or 3 heteroatoms independently selected from N, O and S and optionally being substituted with one or more than one substituents independently selected among the group consisting of halogen, alkyl, halogenoalkyl, alkoxy, aryloxy, halogenoalkoxy, alkylthio, hydroxy, nitro, alkylsulfinyl, alkylsulfonyl, sulfamoyl, N-alkylsulfamoyl, N,N-di-alkylsulfamoyl, alkylsulfonamido and alkylsulfon-N-alkylamido;
the second of radicals R1, R2, R3 represents
  alkyl, optionally substituted with one or more than one substituents independently selected among the group consisting of halogen, cycloalkyl, alkoxy, trifluormethoxy, hydroxy and trifluormethyl;
  cycloalkyl, optionally substituted with one or more than one substituents independently selected among the group consisting of halogen, alkyl, halogenoalkyl, cycloalkyl, alkoxy, halogenalkoxy and hydroxy;
  aryl, optionally substituted with one or more than one substituents independently selected among the group consisting of halogen, alkyl, halogenoalkyl, alkoxy, aryloxy, halogenoalkoxy, alkylthio, hydroxy, nitro, alkylsulfinyl, alkylsulfonyl, sulfamoyl, N-alkylsulfamoyl, N,N-di-alkylsulfamoyl, alkylsulfonamido and alkylsulfon-N-alkylamido; or
  an aromatic or non-aromatic, mono- or bicyclic, optionally benzoannellated, heterocyclic group having 1, 2 or 3, heteroatoms independently selected from N, O and S and optionally being substituted with one or more than one substituents independently selected among the group consisting of halogen, alkyl, halogenoalkyl, alkoxy, aryloxy, halogenoalkoxy, alkylthio, hydroxy, nitro, alkylsulfinyl, alkylsulfonyl, sulfamoyl, N-alkylsulfamoyl, N,N-di-alkylsulfamoyl, alkylsulfonamido and alkylsulfon-N-alkylamido;
the third of radicals R1, R2, R3 represents
  H, alkyl, halogenoalkyl, hydroxyalkyl, —CHO, —COOH, halogen, cyano, alkylsulfonyl, sulfamoyl or B—Y,
  wherein
  B represents alkylene or alkenylene, optionally substituted with hydroxy or alkoxy;
  Y represents —COOH, $SO_3H$, $OPO(OH)_2$, $OP(OH)_2$, —CHO or tetrazolyl; or
the second and the third of radicals R1, R2, R3 represent,
  together with the atom they are attached to, saturated or unsaturated cycloalkyl;
R4-R11, which may be the same or different, represent
  hydrogen, alkyl, hydroxyalkyl, alkoxyalkyl, hydroxy, COOH or acyloxy, where vicinal radicals may also represent bonds or geminal radicals, together with the C atom they are attached to, may also represent carbonyl or cycloalkyl;
R12 represents
  hydrogen, alkyl or phenyl,
and optical isomers, physiologically acceptable salts and derivatives thereof,
for treating or preventing degeneration or destruction of articular cartilage and/or subchondral bone.

The term "alkyl, alkoxy etc." includes linear or branched alkyl groups, such as $CH_3$, $C_2H_5$, n-propyl, $CH(CH_3)_2$, n-butyl, $CH(CH_3)$—$C_2H_5$, isobutyl, $C(CH_3)_3$, n-pentyl or n-hexyl, in particular $CH_3$, $C_2H_5$ or $CH(CH_3)_2$, preferably having—unless otherwise stated—1 to 8, in particular 1 to 6 and more preferably 1 to 4 carbon atoms; as a substituent of a radical R1 to R12 "alkyl, alkoxy etc." preferably comprises 1 to 4 carbon atoms.

Substituted "alkyl, alkoxy etc." includes in particular:

halogenoalkyl, i.e., alkyl, which is partially or completely substituted with fluoro, chloro, bromo and/or iodo, e.g. $CH_2F$, $CHF_2$, $CF_3$, $CH_2Cl$, 2-fluoroethyl, 2-chloroethyl or 2,2,2-trifluoroethyl; as a substituent of a radical R1 to R12 halogenoalkyl preferably means $CHF_2$ and especially $CF_3$;

halogenoalkoxy, i.e., alkoxy, which is partially or completely substituted with fluoro, chloro, bromo and/or iodo, e.g. halogenoalkoxy residues corresponding to the aforementioned halogenoalkyl residues; as a substituent of a radical R1 to R12 halogenoalkoxy preferably means $OCHF_2$ and especially $OCF_3$;

alkoxyalkyl, i.e., alkyl substituted by alkoxy, e.g. —$CH_2$—$OCH_3$ or 2-Methoxyethyl;

hydroxyalkyl, i.e., alkyl which is—preferably mono—substituted by hydroxy, e.g., hydroxymethyl or 2-hydroxyethyl;

trifluoromethylalkyl, i.e. alkyl, which is—preferably mono—substituted by trifluoromethyl, e.g., the residues as described in respect of hydroxyalkyl which are substituted with trifluormethyl instead of hydroxy;

trifluoromethoxyalkyl, i.e. alkyl, which is—preferably mono—substituted by trifluoromethoxy, e.g., the residues as described in respect of hydroxyalkyl which are substituted with trifluormethxy instead of hydroxy;

cycloalkylalkyl, i.e., alkyl, which is—preferably mono—substituted by cycloalkyl, e.g. the residues as described in respect of hydroxyalkyl which are substituted with cyclopropyl, cyclobutyl, cyclopentyl or cyclohexyl instead of hydroxy.

The term "cycloalkyl" includes mono- or bicyclic alkyl groups, such as cyclopropyl, cyclobutyl, cyclopentyl, cyclohexyl, etc., preferably having—unless otherwise stated—3 to 9, in particular 3 to 7 and more preferably 5 or 6 carbon atoms.

The term "alkylene" includes linear or branched alkylene groups, such as methylene and ethylene, preferably having—unless otherwise stated—1 to 8, in particular 1 to 6 and more preferably 1 to 4 carbon atoms. If alkylene is substituted with hydroxyl or alkoxy, monosubstitution is preferred.

The term "alkenylene" includes linear or branched, mono- or polyunsaturated alkylene groups, such as ethenylene, preferably having—unless otherwise stated—2 to 8, in particular 2 to 6 and more preferably 2 to 4 carbon atoms. If alkenylene is substituted with hydroxyl or alkoxy, monosubstitution is preferred.

Acyloxy means —OCOR, wherein R represents alkyl or aryl. Preferred examples are acetyloxy and benzoyloxy.

—COOAlkyl means alkoxycarbonyl, such as CO—$OCH_3$, CO—$OC_2H_5$, CO—$OCH_2$—$C_2H_5$, CO—$OCH(CH_3)_2$, n-butoxycarbonyl, CO—$OCH(CH_3)$—$C_2H_5$, CO—$OCH_2$—$CH(CH_3)_2$, CO—$OC(CH_3)_3$, in particular CO—$OCH_3$, CO—$OC_2H_5$, CO—$OCH(CH_3)_2$ or CO—$OCH_2$—$CH(CH_3)_2$.

—COOAlkPhenyl means an alkoxycarbonyl group which is substituted on the alkyl moiety with phenyl, such as benzyloxycarbonyl.

Alkylthio means —S-Alkyl and is also referred to as alkylsulfanyl or alkylmercapto, such as $SCH_3$, $SC_2H_5$, $SCH_2$—$C_2H_5$, $SCH(CH_3)_2$, n-butylthio, 1-methylpropylthio, 2-methylpropylthio, $SC(CH_3)_3$. Methylthio is preferred.

Alkylsulfinyl means —S(O)-Alkyl and is also referred to as alkylsulfoxo, such as SO—$CH_3$, SO—$C_2H_5$, n-propylsulfinyl, 1-methylethylsulfinyl, n-butylsulfinyl, 1-methylpropylsulfinyl, 2-methylpropylsulfinyl, 1,1-dimethylethylsulfinyl. Methylsulfinyl is preferred.

Alkylsulfonyl means —$S(O)_2$-Alkyl and is also referred to as alkylsulfone, such as $SO_2$—$CH_3$, $SO_2$—$C_2H_5$, n-propylsulfonyl, $SO_2$—$CH(CH_3)_2$, n-butylsulfonyl, 1-methylpropylsulfonyl, 2-methylpropylsulfonyl, $SO_2$—$C(CH_3)_3$. Methylsulfonyl is preferred.

Sulfamoyl means —$S(O)_2NH_2$ and is also referred to as amidosulfonyl or sulfonic acid amid.

N-Alkylsulfamoyl means mono-substituted sulfamoyl —$S(O)_2$NH-Alkyl, e.g. —$S(O)_2$NH—$CH_3$.

N,N-Dialkylsulfamoyl means di-substituted sulfamoyl —$S(O)_2$N-(Alkyl)$_2$, wherein the N-bounded alkyl residues may be the same or different, e.g. —$S(O)_2N(CH_3)_2$.

Alkylsulfonamido means —$NHS(O)_2$-Alkyl, such as $NHSO_2$—$CH_3$, $NHSO_2$—$C_2H_5$, n-propylsulfonamido, $NHSO_2$—$CH(CH_3)_2$, n-butylsulfonamido, 1-methylpropylsulfonamido, 2-methylpropylsulfonamido, $NHSO_2$—$C(CH_3)_3$. Methylsulfonamido is preferred.

Alkylsulfon-N-alkylamido means —$N(Alkyl)S(O)_2$-Alkyl, wherein the N- and the S-bounded alkyl residues may be the same or different, e.g. $N(CH_3)SO_2$—$CH_3$.

Carbonyl, CHO, —COOH, —$SO_3H$ means >C=O, formyl, carboxy, carboxycarbonyl and sulfo, respectively.

"Aryl" preferably means naphthyl and in particular phenyl.

The term "halogen" includes a fluoro, chloro, bromo or iodo atom. Usually fluoro and chloro, and in some cases also bromo are preferred.

"Heterocyclic residues" include in particular 5- or 6-membered heterocyclic residues which may be aromatic or non-aromatic, mono- or bicyclic, and/or benzoannellated. Examples are nitrogen-containing heterocyclic residues, such as pyrrolyl, imidazolyl, pyrazolyl, pyridazinyl, pyrazinyl, indolyl, chinolinyl, especially pyridyl, pyrimidyl and isochinolinyl. The aromatic residues also include heterocyclic residues which contain an oxygen or a sulfur atom, such as thienyl, benzothienyl, furanyl and especially benzofuranyl. Also included are heterocyclic residues which contain 2 or more than 2 different heteroatoms, such as thiazolyl, isothiazolyl, thiadiazolyl, isoxazolyl and oxazolyl. Thienyl, pyridyl and thiazolyl are preferred aromatic heterocyclic residues. Non-aromatic residues include nitrogen-containing heterocyclic residues, such as pyrrolidinyl, piperidinyl and piperazinyl. This also includes heterocyclic residues which contain 2 or more than 2 different heteroatoms, such as morpholinyl.

Substituted residues, in particular alkyl, cycloalkyl, aryl and heteroaryl, are preferably mono-, di- or tri-substituted.

The [α]-annelland may be 6- or especially 5-membered, heterocyclic or especially alicyclic, if alicyclic, then unsaturated or especially saturated, and/or substituted or unsubstituted.

The [α]-annellated pyrrole compounds of Formula (I) include in particular those wherein X represents CR8R9 and A represents a bond between X and the atom carrying radicals R6 and R7 (pyrrolizines); X represents CR8R9 and A represents CR10R11 (indolizines); X represents NR12 and A represents a bond between X and the atom carrying radicals R6 und R7 (pyrrolo[1,2-a]imidazoles); X represents S and A represents a bond between X and the atom carrying radicals R6 and R7 (pyrrolo[2,1-b]thiazoles); X represents S and A represents CR10R11 (pyrrolo[2,1-b]1,3-thiazines); X represents O and A represents CR10R11 (pyrrolo[2,1-b]1,3-oxazines); X represents O and A represents a bond between X and the atom carrying radicals R6 and R7 (pyrrolo[2,1-b]oxazoles), residues not mentioned having the meanings given above.

If the [α]-annelland is a 5-membered unsaturated residue, especially R4 and R6 represent a bond, such as, e.g., in pyrrolizine, pyrrolo[2,1-b]imidazole and pyrrolo[2,1-b]thiazole. If the [α]-annelland is a 6-membered unsaturated residue, especially R4 and R6, such as, e.g., in pyrrolo[2,1-b]1, 3-thiazine, pyrrolo[2,1-b]1,3-oxazine or 5,6-dihydroindolizine, and optionally also R8 and R10, such as, e.g., in indolizine, represent a bond.

Without being bound to a specific [α]-annelland, according to a particular embodiment of the invention, R4-R7 which may be the same or different represent hydrogen or alkyl. According to a further particular embodiment of the invention, at least one of radicals R4, R5, R6 and R7 represents hydroxyalkyl, in particular hydroxymethyl, and the remaining radicals among R4, R5, R6 and R7 independently represent H or alkyl. According to this embodiment it is preferred that R4 is hydroxyalkyl, in particular hydroxymethyl, and R5 is H or alkyl, and R6, R7 independently are H or alkyl. According to a further particular embodiment of the invention, one of radicals R8 and R9 represents H, alkyl, hydroxyalkyl or alkoxyalkyl and the other represents hydroxyl, alkoxy, carboxyl or acyloxy, or R8 and R9 together with the C atom they are attached to, represent a carbonyl group.

6,7-Dihydro-5H-pyrrolizines are especially useful, i.e. compunds of Formula (I), wherein X represents CR8R9, A represents a bond between X and the atom carrying radicals R6 und R7, and R4, R5, R6, R7, R8, R9 which may be the same or different, have the meanings as given above and preferably represent hydrogen or alkyl. 6,7-Dihydro-5H-pyrrolizines wherein R4 to R9 are hydrogen or at least one or two of radicals R4 to R9, for instance R6 und/oder R7, represent alkyl, in particular methyl, are especially preferred.

According to an important aspect of the present invention, compounds of Formula (I), wherein the first and the second of radicals R1, R2, R3, preferably R1 and R2, independently represent an Π-electron-rich system selected from aryl and aromatic heterocyclic residues, in particular phenyl, optionally substituted with one or more than one substituents that in particular are independently selected among the group consisting of halogen, alkyl and halogenoalkyl, in particular CF3, R1 being preferably unsubstituted phenyl and R2 being preferably 4-substituted phenyl, are especially useful.

According to a further important aspect of the invention, compounds of Formula (I), wherein the third of radicals R1, R2, R3, preferably R3, represents an acidic residue such as COOH or B—Y, wherein Y is COOH and B preferably represents alkylene, or represents a precursor of an acidic residue such as B—Y, wherein Y is tetrazolyl, are especially useful.

The use of [6-(4-chlorophenyl)-2,2-dimethyl-7-phenyl-2,3-dihydro-1H-pyrrolizine-5-yl]-acetic acid (ML3000) represented by Formula (Ia):

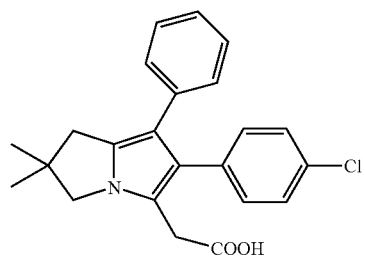

its physiologically acceptable salts and derivatives, e.g., physiologically hydrolysable esters, is especially preferred.

Physiologically acceptable salts include acid or base addition salts.

Acid addition salts are, for instance, salts of compounds of Formula (I) with inorganic acids, such as hydrochloric acid, sulfuric acid, nitric acid or phosphoric acid, or with organic acids, in particular carboxylic acids, e.g. acetic acid, tartaric acid, lactic acid, citric acid, malic acid, amygdalic acid, ascorbic acid, maleic acid, fumaric acid, gluconic acid or sulfonic acid, e.g. methanosulfonic acid, phenylsulfonic acid and toluenesulfonic acid, and the like.

Base addition salts are, for instance, salts of compounds of Formula (I) with inorganic bases, such as sodium or potassium hydroxide or with organic bases, such as mono-, di- or triethanolamine, and the like.

Physiologically acceptable derivatives include in particular prodrugs of the compounds of formula (I) which are reconverted in vivo to the compounds of formula (I) or an active form thereof (metabolite). Examples are hydrolysable esters of the compounds of formula (I) wherein the third of radicals R1, R2, R3 represents an acidic residue, e.g. alkyl (the third of radicals R1, R2, R3 comprising the functionality COOAlkyl), aralkyl (the third of radicals R1, R2, R3 comprising the functionality COOAlkaryl, e.g., COOAlkPhenyl), pivaloyloxymethyl, acetoxymethyl, phthalidyl, indanyl and methoxymethyl esters thereof.

According to a particular aspect, the present invention relates to the use of chondroprotective agents which are selected among the compounds of Formula (I).

The term "chondroprotective agent" as used herein will be understood to refer to those compounds whose chief site of action is the cartilage. It will also be appreciated that such chondroprotective agents may also possess anti-inflammatory action with regard to the synovium, may positively impact the biosynthesis of cells in subchondral bone and other connective tissues such as synovial fibroblasts, and may mediate inflammatory cell migration so as to impede the inflammatory process.

The present invention provides methods of treatment, and pharmaceutical compositions useful therein as well as suitable packaging therefor, which are applicable to mammals which suffer from or in the future may suffer from injury, damage or loss of articular cartilage and/or subchondral bone in one or more joints of such a mammal.

Using the compounds of Formula (I) has particular advantages over other NSAIDs, especially those more established in use, which may actually exacerbate the progress of osteoarthritis, especially when long-term application is indicated. It is surprising that the compounds of Formula (I) are useful in treating or preventing such articular cartilage damage while simultaneously having no adverse impact on the course of inflammation in the mammal joint involved.

The ability of the compounds of formula (I) to reverse the disease process which ultimately leads to articular cartilage and/or subchondral bone destruction and loss has far-reaching implications for the safe and effective treatment of mammals, especially those which are in the early stages of articular cartilage and/or subchondral bone degeneration or destruction.

As used herein, the term "mammal(s)" denotes any mammal, preferably humans, cat, dog or horse, of which there are a large number of different breeds.

In accordance with the present invention, treating or preventing the degeneration or destruction of articular cartilage and/or subchondral bone in one or more joints of a mammal in need of such treatment, comprises administering to said mammal an amount therapeutically effective for treating or preventing said degeneration or destruction of articular cartilage and/or subchondral bone, of one or more than one compound of Formula (I).

Said treatment or prevention especially comprises ameliorating, diminishing, actively treating, reversing or preventing any degeneration or destruction, e.g. injury, damage or loss, of articular cartilage and/or subchondral bone, especially subsequent to said early stages of said degeneration or destruction. The expression "treating or preventing" as used herein with reference to the administration of the chondroprotective compounds of the present invention, is intended to refer to both the therapeutic objective of said administration as well as the therapeutic results actually achieved by said administration. As above-discussed, the extent of therapy accomplished by administration of said compounds may range from an amelioration to a significant diminishing of the course of the disease, and beyond to active treatment of the disease, including a reversal of the disease process. The higher degrees of therapeutic effectiveness result in the prevention of any injury, damage or loss of articular cartilage and/or subchondral bone subsequent to the early stages of degeneration in said articular cartilage and/or subchondral bone.

The expression "the early stages of degeneration in articular cartilage and/or subchondral bone" is intended to mean the very beginning of the initial pathologic changes in the articular cartilage and/or subchondral bone which define and are the result of a disease process.

Cartilage is a fibrous connective tissue existing in several forms, e.g., hyaline cartilage, elastic cartilage, and fibrocartilage. It is a connective tissue comprising water, collagen and proteoglycans which together create a unique fiber-reinforced water gel which is stiff but resilient and has considerable shock-absorbing capacity. Articular cartilage is cartilage to be found in the joints of mammals. It comprises living cells (chondrocytes) which generate and are surrounded by the interstitial material generally referred to as the extracellular matrix. Chondrocytes producing the extracellular matrix of the cartilage are highly active, and the integrity of this matrix is maintained by an equilibrium between the actions of the catabolic cytokines IL-1$\alpha$, $\beta$ and TNF$\alpha$ and the anabolic cytokines IGF and TGF$\beta$. IL-1$\alpha$, $\beta$ and TNF$\alpha$ act by inducing the production of specific matrix degrading metalloproteases, while IGF and TGF$\beta$ act as growth factors by inducing the production of the macromolecular building blocks of cartilage, collagen and the proteoglycans. Other cytokines and their inhibitors, as well as tissue inhibitors of metalloprotease (TIMP), also influence this equilibrium, referred to as matrix homeostasis.

The term "metalloprotease" as used herein is intended to refer to the matrix metalloproteases (MMPs), especially including those in this family of enzymes which usually exhibit elevated concentrations during articular cartilage degeneration, i.e., the stromelysins, the collagenases, and the gelatinases. Collagenase is generally responsible for the degradation of native collagen; stromelysin is generally responsible for the degradation of the proteoglycans; and gelatinase is generally responsible for the degradation of denatured collagen. An enzyme with MMP properties, aggrecanase, is also included within this term, since it is responsible for the proteolysis of cartilage proteoglycan aggregates which are present during the early stages of cartilage degeneration. The three collagenases present in articular cartilage during the early stages of degeneration are collagenase-1 (MMP-1), collagenase-2 (MMP-8), and collagenase-3 (MMP-13). Of the three stromelysins, stromelysin-1 (MMP-3), stromelysin-2 (MMP-10), and stromelysin-3 (MMP-11), only stromelysin-1 appears in articular cartilage during the early stages of its degeneration.

Since osteoarthritis is defined as the failure of the diarthrodial (movable, synovial-lined) joint, it follows that in such a joint there will always be found at least two movable bony surfaces that would meet but for the fact that they are surrounded by the synovial membrane, which secretes synovial fluid, a transparent alkaline viscid fluid which fills the joint cavity, and articular cartilage, which is interposed between the articulating bony surfaces, usually in place of the synovial membrane at that point.

The earliest gross pathologic finding in osteoarthrits is softening of the articular cartilage in habitually loaded areas of the joint surface, which in the case of the knee joint of the mammal, especially in models of osteoarthritis involving transection of the cruciate ligament in the knee joint, consists of the femoral condyle and the tibial plateau. With progression of osteoarthritis the integrity of the cartilage surface is lost and the articular cartilage thins, with vertical clefts extending into the depth of the cartilage in a process called fibrillation. Joint motion may cause fibrillated cartilage to shed segments that expose the bone underneath (subchondral), which then undergoes sclerosis. Subchondral cysts also develop which may be filled with synovial fluid. At the joint margins osteophytes (bone spurs) form.

Changes in the subchondral bone also play a role in the pathology of cartilage degeneration and destruction. Studies of the joints of mammals, especially dogs, which have undergone anterior cruciate ligament transection reveals subchondral sclerosis and osteopenia, i.e., bone loss in the subchondral trabeculae. Subsequent to these changes, there is a thickening of the subchondral plate. The loss of subchondral bone increases the mechanical strain on the overlying articular cartilage, leading to its degeneration. The subsequent thickening of the subchondral plate negatively affects intrinsic repair mechanisms and thereby contributes to the progression of cartilage breakdown.

The breakdown of the extracellular matrix of the cartilage is accompanied by mitotic division of the chondrocytes which then form in clusters. There is a reduction in the glycosaminoglycan components of the cartilage and patchy proteoglycan depletion. In many areas fibrocartilage, characterized by an extracellular matrix of thick, compact parallel collagenous bundles, replaces hyaline cartilage. However, it should be noted that these and the above-described pathologic changes in the articular cartilage are characteristic of later stages of osteoarthritis, and that hypertrophy, i.e., thickening of the articular cartilage occurs first, as shown by the cruciate-deficient mammal, especially dog knee joint model. Cartilage thickening results from increased water content, an increase in proteoglycan synthesis, and an Increase in both the content and concentration of proteoglycans in the articular cartilage. This stage of hypertrophic repair of the articular cartilage may persist for some time, but the repair cartilage tissue which is formed lacks the resiliency and resistance to mechanical stress possessed by normal hyaline cartilage. Eventually, proteoglycan production subsides and the chondrocytes are no longer able to maintain their extracellular matrix. This end stage results in full-thickness loss of articular cartilage.

The early stages of the pathologic changes leading to cartilage injury and loss involve attempted repair through increased synthesis of matrix macromolecules. The makeup of the repair cartilage is deficient however, due to altered composition and distribution of the glycosaminoglycan component and a change in its capacity to aggregate with the hyaluronic acid component. Particles released during these pathologic changes may also lead to inflammatory changes in the synovial membrane. However, despite this ongoing pathology, the initial stages of cartilage injury and loss may be asymptomatic with relatively little pain. Accordingly, an appropriate objective is to identify those extracellular matrix components and cytokines for which measurable changes may be identified which profile a mammal subject in the early stages of cartilage injury and loss before focal cartilage loss can be identified radiographically. Meeting this objective will permit diagnostic classification of mammals which are candidates for early pharmacological intervention before significant cartilage degeneration occurs.

Said pathologic changes in the articular cartilage include changes in the composition, form and density of the articular cartilage from that present before the onset of said disease process, which result in a degradation of the beneficial properties of said articular cartilage including strength, resilience, elasticity, conformational integrity and stability, viability, and the ability to successfully resist various kinds of mechanical stress, especially the ability to absorb mechanical shocks. These pathologic changes in composition especially include changes in the type and amount of glycosaminoglycans and collagen fibers present in the articular cartilage.

Pathologic changes in the subchondral bone include sclerosis thereof, increasing density with decreasing resilience and elasticity thereof, and a diminishing ability to successfully resist various kinds of mechanical stress, especially the ability to absorb mechanical shocks. These pathologic changes especially include improper repair of trabecular microfractures with trabecular thickening, and pathogenic changes in osteoblastic metabolite production and differentiated phenotype.

Synovitis, i.e., inflammation of the synovium, the synovial membrane, can contribute to the pathology of cartilage injury and loss. Synovial inflammation is characterized by extensive infiltration of the synovial fluid by mono-nuclear cells, by synovial membrane cell hyperplasia, and by lymphoid aggregates. Synovitis contributes significantly to cartilage injury in rheumatoid and other inflammatory arthropathies. The role of synovial inflammation in the early stages of OA are less well understood, however synovitis is present at the clinical stage of OA.

According to one aspect of the present invention, the use of compounds of Formula (I) is directed to treating or preventing the degeneration or destruction of articular cartilage and/or subchondral bone, wherein said degeneration or destruction is associated with osteoarthritis. In particular, said use is directed to treating or preventing the pathologic changes involved therewith. Thus, the present invention also relates to the treatment of osteoarthritis, wherein said treatment is accompanied by a therapeutically useful impact on articular cartilage and/or subchondral bone.

Treating or preventing the degeneration or destruction of articular cartilage and/or subchondral bone may also comprise administering in addition to one or more than one compound of Formula (I), one or more members selected from the group consisting essentially of polysulfated glycosaminoglycan (PSGAG), glucosamine, chondroitin sulfate (CS), hyaluronic acid (HA), pentosan polysulfate (PPS), doxycycline, and minocycline.

Further, the compounds of Formula (I) of the present invention may also be combined with other therapeutically active ingredients which would be readily apparent to the skilled artisan in this field, and which will usually be determined by the circumstances under which the therapeutic agent of the present invention is administered. For instance, where a joint has become seriously infected at the same time by microorganisms, e.g., bacteria, fungi, protozoa, virus and the like, the active ingredient of the present invention will desirably be administered in combination with one or more antibiotic, antifungal, antiprotozoal, antiviral or similar therapeutic agents. Also, the active ingredient of the present invention may be administered in combination with NSAIDs as well with inhibitors of other mediators of inflammation. Additional classes of such inhibitors and examples thereof include, e.g., $H_1$-receptor antagonists; kinin-$B_1$- and $B_2$-receptor antagonists; prostaglandin inhibitors such as PGD-, PGF-PGI$_2$-, and PGE-receptor antagonists; thromboxane $A_2$ (TXA2)-inhibitors; PAF-receptor antagonists; gold in the form of an aurothio group together with various hydrophilic groups; immunosuppressive agents, e.g., cyclosporine, azathioprine, and methotrexate; anti-inflammatory glucocorticoids, e.g., dexamethasone; broad-spectrum antiparasitic antibiotics, e.g., the avermectins and the milbemycins; penicillamine; hydroxychloroquine; anti-gout agents, e.g., colchicine, xanthine oxidase inhibitors, e.g., allopurinol, and uricosuric agents, e.g., probenecid, sulfinpyrazone, and benzbromarone.

Because the early stages of articular cartilage degeneration are prevalent among geriatric mammals, it will be appreciated by those skilled in the art that the compounds of Formula (I) may also be administered in combination with therapeutic agents intended for the treatment of disease conditions, syndromes and symptoms which are also found in abundance in older mammals. Such therapeutic agents and the conditions which they are used to treat include, e.g., cognitive therapeutics to counteract memory loss and impairment; and antidyskinetic/antiparkinsonian agents, e.g., selegeline. Another large class of such therapeutic agents includes anti-hypertensives and other cardiovascular drugs intended to offset hypertension, myocardial ischemia including angina, congestive heart failure, and myocardial infarction, e.g., diuretics, vasodilators such as hydralazine, β-adrenergic receptor antagonists such as propranolol, angiotensin-II converting enzyme inhibitors (ACE-inhibitors) such as enalapril used to treat geriatric mammals with mitral insufficiency, and enalapril alone and in combination with neutral endopeptidase inhibitors, angiotensin II receptor antagonists such as losartan, renin inhibitors, calcium channel blockers such as nifedipine, sympatholytic agents such as methyldopa, $α_2$-adrenergic agonist such as clonidine, α-adrenergic receptor antagonists such as prazosin, and HMG-CoA-reductase inhibitors (anti-hypercholesterolemics) such as lovastatin or atorvastatin. Still other classes of such therapeutic agents include antineoplastic agents, especially antimitotic drugs including the vinca alkaloids such as vinblastine and vincristine, for treating various cancers; therapeutic agents for treating renal failure; anti-obesity drugs for treating excess weight problems in mammals; anti-parasitic drugs for treating both endo- and ecto-parasites which commonly afflict mammals; and anti-pruritic drugs for treating various types of pruritis in mammals.

Other types of drugs which can be used in combination with the anti-inflammatory agents of the present invention include growth hormone secretagogues; strong analgesics; local and systemic anesthetics; and $H_2$-receptor antagonists and other gastroprotective agents. It will be recognized by those of ordinary skill in this art that some of the above combinations of therapeutic agents will be used most frequently to treat various acute conditions in mammals, e.g., bacterial infections occurring simultaneously with degenerative joint disease. However, there would be an equal if not greater interest on the part of such skilled persons in treating chronic conditions in mammals.

In accordance with a regimen which would be used for this purpose, it is contemplated that the compounds of Formula (I) would be administered in combination with other medications used on a regularly scheduled basis for treating chronic conditions such as hyperlipidemia. It is also envisioned that administration in combinations could assume a number of different forms and still be within the scope of the present invention. For example, the compounds of Formula (I) might simply be formulated with one or more of the other therapeutic agents which are to form the intended combination, into a convenient dosage form, such as an oral tablet, containing all of the drugs forming the combination. Varying half-lives for the different drugs could be accommodated by the person skilled in preparing formulations by creating controlled-release forms of said drugs with different release times so that relatively uniform dosing was achieved. A medicated feed used as the dosage form could also be prepared in accordance with well known principles in the art of formulation, in which the drugs used in the combination were simply present together in admixture in the feed composition. The present invention also contemplates co-administration in which the combination of drugs is achieved by the simultaneous administration of the drugs to be given in combination. Such co-administration could even be by means of different dosage forms and routes of administration. The present invention further contemplates the use of such combinations in accordance with different but regular and continuous dosing schedules whereby desired plasma levels of the drugs involved were maintained in the mammal being treated, even though the individual drugs making up the combination were not being administered to said mammal simultaneously. All such combinations would be well within the skill of the art to devise and administer.

When the compounds of Formula (I) are to be used as active ingredients in the methods and compositions of the present invention, they can be incorporated into standard pharmaceutical dosage forms. Thus, the present invention also relates to pharmaceutical compositions comprising a pharmaceutically acceptable carrier and an amount therapeutically effective for treating or preventing said degeneration or destruction of articular cartilage and/or subchondral bone, of a compound of Formula (I) as above-defined. For example, they are useful when administered in systemic or local, oral or parenteral applications and for this purpose are combined with the usual pharmaceutical excipients, diluents and adjuvants, e.g., organic and inorganic inert carrier materials such as water, gelatin, lactose, starch, magnesium stearate, talc, vegetable oils, gums, polyalkyleneglycols, etc. These pharmaceutical preparations can be employed in a solid form, e.g., as tablets, capsules, and especially in combination with or for admixture with a palatable food item suitable for mammals; or they can be administered in liquid form, e.g., as solutions and elibdrs. Pharmaceutical excipients and adjuvants which can be added include preservatives, antioxidants, antimicrobial agents and other stabilizers; wetting, emulsifying, and suspending agents, and anticaking compounds; fragrance and coloring additives; compositions for improving compressibility, or to create a delayed-, sustained-, or controlled-release of the active ingredient; and various salts to change the osmotic pressure of the pharmaceutical preparation or to act as buffers. Particular dosage forms which have been used with success include a 5% mixed-micelle solution of ML3000 for intravenous injection, a 3% palatable paste, and oral tablets.

The therapeutically effective amount of a compound of Formula (I) as defined may be administered systemically to said mammal, wherein said systemic administration comprises: (1) injection or infusion into suitable body tissues or cavities of a pharmaceutical composition containing said compound in suitable liquid form such as aqueous solutions, emulsions or suspensions for intraarterial, intra- or transdermal (including subcutaneous), or intraspinal especially intrathecal and most commonly intramuscular or intravenous delivery thereof; or for serving as a depot for delivery thereof; (2) instillation into suitable body tissues or cavities of a pharmaceutical composition containing said compound in suitable solid form, e.g., comprising a matrix of bio-compatible and bio-erodible materials in which particles of a solid chondroprotective compound of Formula (I) are dispersed, or in which, possibly, globules or isolated cells of a liquid chondroprotective compound of Formula (I) are entrapped, for serving as a solid implant composition for delayed-, sustained-, and/or controlled-release delivery thereof; or (3) ingestion or administration of a pharmaceutical composition containing said compound in suitable solid or liquid form for transdermal delivery thereof, for instance a transdermal patch or a subepidermal (subcuticular) implant, for peroral delivery thereof.

A substantial number of the dosage forms described herein may be formulated so as to provide controlled-, sustained-, and/or delayed release of the active ingredient from said dosage form.

A useful controlled release dosage form of ML3000 in accordance with the present invention is one which maintains a ML3000 plasma level greater than 100 ng/mL for most of the day after a single oral dose at 5 mg/kg. Preferred oral controlled release dosage forms of ML3000 in accordance with the present invention are ones which maintain a plasma ML3000 concentration greater than 100 ng/mL for a period of time greater than that for which an immediate release dosage form of ML3000 maintains a comparable plasma level, when said immediate release dosage form and controlled release dosage form are administered at the same dose.

Immediate release ML3000 dosage forms containing doses of 2.5 and 5 mg/kg maintain a plasma ML3000 concentration above 100 and 200 ng/mL for 8 hours, respectively.

Preferred peroral dosage forms for systemic administration are solids, e.g., palatable oral compositions such as fast dissolving palatable wafers, tablets, capsules, caplets, etc., and liquids, e.g., solutions, suspensions, emulsions, etc. Pharmaceutical compositions of special types suitable for oral administration to mammals may be used, and include, but are not limited to such items as an oral paste to be delivered to the back of the tongue of the mammal being treated, a granular form to be delivered through incorporation in the mammal's food, and a chewable form wherein the active ingredient is consumed along with the palatable chew, or a chewable form which may deliver the active ingredient by leaching from the body of the chew which is not consumed, during mastication by the mammal being treated.

Said therapeutically effective amount of a compound of Formula (I) as defined may also be administered locally to said mammal, wherein said local administration comprises: (1) injection or infusion into a local site of degeneration or destruction of articular cartilage and/or subchondral bone of a pharmaceutical composition containing said compound of formula (I) in suitable liquid form for delivery thereof, including components which provide delayed-release, controlled-release, and/or sustained-release of said compound into said local site; or for serving as a depot for delivery thereof wherein said composition provides storage of said compound and thereafter delayed-, sustained-, and/or controlled-release thereof; or (2) instillation of a pharmaceutical composition containing said compound in suitable solid form for serving as a solid implant for delivery thereof, said composition optionally providing delayed-, sustained-, and/or controlled-release of said compound to said local site.

Local administration is focused on suitable articular tissues into which the chondroprotective compound of Formula (I) may be injected, infused, implanted, deposited, inserted, or instilled. Such administration may include, but is not limited to, that which is intraarticular, intrachondrial, intracostal, intraligamentous, intramedulary, intramuscular, intraosteal, intrapelvic, intraspinal, intrasternal, intrasynovial, intratarsal, intrathecal, or intravenous.

Pharmaceutical compositions in liquid form containing the chondroprotective compound of Formula (I) offer the advantage of permitting injections of the liquid into or in close proximity to the articular site. By injection of the compound of Formula (I) directly into the joint, it is possible to achieve a high concentration of said compound in a short period of time, thus not only substantially enhancing access of said compound to the joint tissues, and thus the therapeutic activity of the compound of Formula (I), but also at the same time minimizing the occurrence of untoward adverse reactions that might otherwise occur. The result is a high local concentration of the compound of Formula (I) with a correspondingly low systemic carryover concentration.

Injections may also be made of pharmaceutical compositions containing the chondroprotective compound of Formula (I), where the pharmaceutical composition is in delayed-release, controlled-release, or sustained-release form. These formulations of recognized composition may be a solids, semi-solids, gels or other liquid/solid combinations in which an erodible matrix or series of coatings is used to provide a continuous release of the compound of Formula (I) at a predetermined rate or at variable rates if desired. The terms "extended-release" and "long-acting" as well as others are used to describe these formulations. All of these employ various combinations of bioerodible polymers, e.g., various cellulosic polymers, and natural materials, e.g., cornstarch and magnesium stearate, to obtain slow and/or uniform dispensing of the compound of Formula (I) contained within the matrix. These pharmaceutical compositions may be injected into the articular site if suitably liquid or suspendable, or may be delivered by other means if more solid in nature.

The therapeutically effective amount for treating or preventing articular cartilage and/or subchondral bone degeneration or destruction, of the compound of Formula (I), is administered to a mammal being treated in an amount expressed as milligrams per kilogram of body weight of said mammal, per day: "mg/kg/day". The expression "per day" as used herein should not be interpreted as necessarily requiring that any particular dosage form be administered on a daily basis to the mammal being treated. The expression "per day" is merely an indication of the smallest convenient but arbitrary segment of time which is being used as part of the overall unit for measuring the dose of chondroprotective compound being administered. The dose, i.e., the therapeutically effective amount of a compound of Formula (I) for treating or preventing articular cartilage and/or subchondral bone degeneration or destruction will usually range from about 0.1 mg/kg/day to about 20.0 mg/kg/day, preferably from about 0.1 mg/kg/day to about 12.0 mg/kg/day, more preferably from about 0.5 mg/kg/day to about 10.0 mg/kg/day, and most preferably from about 0.5 mg/kg/day to about 8.0 mg/kg/day. Typical dosage forms and amounts for ML3000 would include oral administration of ML3000 at a dose rate of 2.5-5.0 mg/kg/day of body weight.

It is necessary for the skilled artisan, not only to determine the preferred route of administration and the corresponding dosage form and amount, but said artisan must also determine the dosing regimen, i.e., the frequency of dosing. In general terms it is most likely that the choice will be between once-a-day (s.i.d.) dosing and twice-a-day (b.i.d.) dosing, and that the former will provide more rapid and profound therapy, while the latter will provide less profound but more sustained therapy. However, this generalization does not take into account such important variables as the specific type of articular cartilage or subchondral bone degeneration or destruction involved, the specific therapeutic agent involved and its pharmacokinetics, and the specific patient (mammal) involved. For an approved product in the marketplace, much of this information is already provided by the results of clinical studies carried out to obtain such approval. In other cases, such information may be obtained in a straightforward manner in accordance with the teachings and guidelines contained in the instant specification taken in light of the knowledge and skill of the artisan. The results which are obtained can also be correlated with data from corresponding evaluations of an approved product in the same assays.

It is also contemplated that in accordance with the present invention there will also be provided a package suitable for use in commerce for treating or preventing the degeneration or destruction of articular cartilage and/or subchondral bone in one or more joints of a mammal in need of such treatment, comprising a suitable outer carton and an inner container removably housed therein; enclosed in said container a suitable dosage form of a compound of Formula (I) as described hereinabove; and associated with said carton or container printed instructional and informational material, which may be attached to said carton or to said container enclosed in said carton, or displayed as an integral part of said carton or container, said instructional and informational material stating in words which convey to a reader thereof that said active ingredient, when administered to a mammal in a condition of degeneration or destruction of articular cartilage and/or subchondral bone in one or more joints thereof, will ameliorate, diminish, actively treat, reverse or prevent any injury, damage or loss of articular cartilage or subchondral bone. In a preferred embodiment said package comprising carton and container as above-described will conform to all regulatory requirements relating to the sale and use of drugs for the treatment of animals, including especially said instructional and informational material.

It is also contemplated that in accordance with the present invention there will further be provided a package of the type described immediately above, comprising a suitable container as described; enclosed in said container an oral dosage form of a compound of Formula (I); and associated with said container printed instructional and informational material as above-described.

The method of the present invention can be further defined to comprise two basic steps: (I) establishing the status of a candidate mammal as presently or prospectively being in a condition of degeneration or destruction of articular cartilage and/or subchondral bone in one or more joints of said mammal, thereby confirming that said mammal is in need of such treatment; and thereupon (II) treating or preventing said condition by administering to said mammal an amount therapeutically effective for treating or preventing said degeneration or destruction of articular cartilage and/or subchondral bone, of a chondroprotective compound of Formula (I). The various aspects of Step (II) have already been discussed above in detail. Accordingly, the aspects of Step (I) will now be discussed in detail.

As far as diagnosis is concerned, it is expedient to establish the status of a mammal which is a candidate for treatment in accordance with the present invention as to whether or not the mammal is presently or prospectively in a condition of degeneration or destruction of articular cartilage and/or subchondral bone in one or more joints of said mammal. The expression "presently or prospectively" as used herein is intended to mean that in accordance with the below-discussed methods of making that determination, it is possible to identify a candidate mammal as either being presently in need of such treatment, or as very likely or expected to be in need of such treatment in the short term future. Prospective need of treatment may be established by those determinations of positive factors which from the experience of the artisan lead directly to the condition of articular cartilage and/or subchondral bone degeneration or destruction. For example, the artisan may establish from clinical examination of a mammal that it has incipient hip dysplasia, and may confirm this conclusion with radiographic evidence from which it may be determined in accordance with established methods of measurement that the mammal will develop hip dysplasia within the short term future.

The status of said mammal as presently or prospectively being in said condition of degeneration or destruction and especially in said early stages, and thus in need of such treatment, is in particular determined by:

(A) positive results from the clinical arthroscopic examination and evaluation of the joints of the candidate mammal. The diagnosis of incipient or realized hip dysplasia has already been discussed. Other clinical symptomology and signs would include those gained from direct examination of the joints of the candidate mammal;

(B) performance of any invasive surgical procedure on one or more joints of the candidate mammal which would be under most circumstances be sufficient reason by itself to conclude that treatment was needed. This follows from the fact that invasive surgery on the joint of a mammal inevitably degrades the ability of that joint to bear its accustomed load as efficiently as before surgery. The increased mechanical stress on the joint would, in the experience of the skilled artisan, lead directly to the early stages of articular cartilage and/or subchondral bone degeneration. Such surgery on the joint would also produce an effusion of blood and other fluids containing cytokines and other factors which are causative agents of inflammation, and would thereby permit their migration and absorption into the solid tissues of the joint, including the cartilage and/or subchondral bone. The artisan would appreciate that this would also lead directly to the early stages of articular cartilage and/or subchondral bone degeneration;

(C) positive results from an examination of one or more joints of said mammal using noninvasive procedures including radiographic and magnetic resonance imaging (MRI). The latter technique is better for evaluating soft tissues than is the former. MRI is a technique for multiplanar body imaging that shows increased soft tissue contrast resolution. Since MRI can visualize soft tissue changes, it is suitable for imaging the pathology of the early changes in articular cartilage and subchondral bone degeneration;

(D) positive results from any biochemical test performed on body fluids or joint tissue of the candidate mammal with respect to one or more of the following substances: increased interleukin-1 beta (IL-1β); increased tumor necrosis factor alpha (TNFα); increased ratio of IL-1β to IL-1 receptor antagonist protein (IL-1Ra); increased expression of p55 TNF receptors (p55 TNF-R); increased interleukin-6 (IL-6); increased leukemia inhibitory factor (LIF); unchanged or decreased insulin-like growth factor-1 (IGF-1); decreased transforming growth factor beta (TGFβ); unchanged or decreased platelet-derived growth factor (PDGF); unchanged or decreased basic fibroblast growth factor (b-FGF); increased keratan sulfate; increased stromelysin; increased ratio of stromelysin to tissue inhibitor of metalloproteases (TIMP); increased osteocalcin; increased alkaline phosphatase; increased cAMP responsive to hormone challenge; increased urokinase plasminogen activator (uPA); increased cartilage oligomeric matrix protein; and increased collagenase.

IL-1, which occurs as IL-1α and IL-1β, is a catabolic cytokine which mediates articular cartilage injury and loss in mammal joints. It acts by suppressing the synthesis of type II collagen found in articular cartilage while promoting the synthesis of type I collagen characteristic of fibroblasts; by inducing the production of enzymes involved in matrix degradation; and by suppressing the ability of chondrocytes to synthesize new proteoglycans. The number of IL-1 receptors on the surface of chondrocytes in articular cartilage in the early stages of degeneration which must be occupied in order to elicit catabolic enzyme production is only one-fourth as great as that required normally (1% vs. 4%). IL-1 and its modulator IL-1Ra are produced in an autocrine and paracrine fashion by the same synovial macrophages, and IL-1 Ra production may be increased in the presence of granulocyte macrophage colony-stimulating factor (GM-CSF). However, there is a significant disparity between IL-1 and IL-1Ra potency, with approximately 130-fold more IL-1Ra being required to abolish the effects of IL-1, as measured in chondrocytes and cartilage explants. Any imbalance between IL-1 and IL-1Ra will further exacerbate the degeneration of articular cartilage.

Consequently, it is also an appropriate objective to measure levels of IL-1 and IL-1Ra and their ratios in mammals in the early stages of articular cartilage degeneration, and the same values in mammals not so afflicted so that measurable changes may be identified which profile a mammal subject in the early stages of cartilage injury and loss before focal cartilage loss can be identified radiographically. These results provide diagnostic classification of mammals which are candidates for early pharmacological intervention before significant cartilage degeneration occurs. Furthermore, the proportion of IL-1α and IL-1β-secreting macrophages occurring in the synovial fluid and synovial tissue of a joint in the early stages of articular cartilage degeneration can be detected and is significantly greater than the proportion of similar cells isolated from synovial fluid and synovial tissue from normal joints, i.e., joints which are not in the early stages of articular cartilage degeneration. Here again, these results provide diagnostic classification of mammals which are candidates for early pharmacological intervention before significant cartilage degeneration occurs.

Further still, changes in subchondral bone occur before gross alterations in the articular cartilage become apparent because cytokines responsible for initiating and maintaining the inflammatory process gain access to the lower layers of cartilage through microcracks across the calcified zone. The metabolism of the chondrocytes involved is adversely affected, and in addition the chondrocytes in the middle zone of the articular cartilage produce many cytokines, including those responsible for initiating and maintaining the inflammatory process. These chondrocytes, acting in an autocrine fashion, thus contribute to the destruction of their own extracellular matrix. The increased water content of the articular cartilage also facilitates this process by increasing diffusion of the inflammatory cytokines throughout the matrix. It is, consequently, an appropriate objective to measure levels of various inflammatory cytokines produced by chondrocytes, synovial cells, and/or subchondral osteocytes in mammals, especially canines during the process of articular cartilage degeneration, and the same values in mammals not so afflicted so that measurable changes may be identified which profile a mammal subject in the early stages of cartilage injury and loss before focal cartilage loss can be identified radiographically. These results provide diagnostic classificaton of mammals which are candidates for early pharmacological intervention before significant cartilage degeneration occurs.

Tumor necrosis factor alpha (TNFα) has only one-tenth the potency of IL-1 with regard to the degeneration of articular cartilage, but its concentration in synovial fluid significantly increases in the knee joints of mammals, especially with sectioned cruciate ligaments compared to the opposite, unoperated knee. There is also enhanced expression of p55 TNF receptors (TNF-R) on chondrocytes isolated from articular cartilage present in such knee joints. Accordingly, since TNFα plays a role in the pathologic changes which take place in the early stages of cartilage injury and loss, it is likewise an appropriate objective to measure levels of TNFα and TNF-R in the joints of mammals in the early stages of articular cartilage degeneration, and the same values in mammals not so afflicted so that measurable changes may be identified which profile a mammal subject in the early stages of cartilage injury and loss before focal cartilage loss can be identified radiographically. These results provide diagnostic classification of mammals which are candidates for early pharmacological intervention before significant cartilage degeneration occurs.

Interleukin-6 (IL-6) is a multifunctional cytokine, but plays an inflammatory role and is found in elevated levels in joints and synovial fluid from damaged as compared to control limbs. IL-6 is also responsible for enhanced expression of TNF-R on chondrocytes and increased proteoglycan production by chondrocytes, as well as induction of glycosaminoglycan release. Measurement of IL-6 levels in joints, synovial fluid and chondrocytes of mammal joints in the early stages of articular cartilage injury and loss, compared to control, can be used as a diagnostic tool for identifying mammals that are appropriate candidates for pharmacological treatment, before any focal cartilage loss is evident from radiographic examination.

Leukemia inhibitory factor (LIF) is produced by monocytes, granulocytes, T cells, fibroblasts, and other cell types associated with inflammatory conditions. Synoviocytes and chondrocytes synthesize and secrete LIF in the presence of IL-1β and TNFα. Thus, measurement of comparative increases in levels of LIF can be used diagnostically to select mammal candidates for pharmacologic treatment of the early stages of articular cartilage injury and loss.

The degeneration, injury and loss of articular cartilage in mammals is caused by an imbalance between the cytokines that drive the above-described catabolic processes and those cytokines which are responsible for maintaining the synthetic and proliferative responses of the chondrocytes in the cartilage. Insulin-like growth factor (IGF-1), transforming growth factor beta (TGFβ), platelet-derived growth factor (PDGF), and fibroblast growth factor, e.g., basic fibroblast growth factor (bFGF), are all mitogenic with respect to the chondrocytes and stimulate matrix synthesis in articular cartilage.

Insulin-like growth factor (IGF) exists as types I and II, and IGF-I is a potent mediator of cartilage synthesis. Furthermore, it reduces degradation and promotes synthesis of proteoglycans even in the presence of IL-1β and TNFα. Serum levels of IGF-1 are maintained by high-affinity binding proteins (IGF-BPs) and IGF-1 is important in both bone and cartilage turnover. Levels of IGF-1 compared to control permit diagnostic evaluation of mammal candidates for early pharmacologic treatment of articular cartilage degeneration.

Transforming growth factor (TGFβ) is produced by chondrocytes and is a powerful mitogen for the turnover of both cartilage and bone. Further, it stimulates the synthesis of matrix and has anti-inflammatory activity. It also inhibits the degradation of the matrix by stimulating protease inhibitor production, and blocking collagenase and metalloprotease release. Further still, it promotes cartilage repair by stimulating production of collagen, fibronectin, inhibitors of plasminogen activators, and tissue inhibitors of metalloproteases (TIMP) by various cells in the mammal joint. Synovial fluid levels of TGFβ are low in the joints of mammals in the early stages of articular cartilage injury and loss. Consequently, levels of TGFβ compared to control permit diagnostic evaluation of mammal candidates for early pharmacologic treatment of articular cartilage degeneration.

With the progressive degeneration, i.e., catabolism of the articular cartilage in the mammal joint, a number of metabolites are produced which are useful as markers of the cartilage degeneration, both as to its occurrence and as to its advance. For example, degradation of cartilage by IL-1α and IL-1β or TNFα releases glycosaminoglycans (GAGS), which can be measured in the synovial fluid of a mammal being tested. Furthermore, GAG levels change after treatment so that it is possible to monitor the course of pharmacologic intervention, using synovial fluid GAG levels as a marker of articular cartilage turnover.

Since the degradation of articular cartilage involves collagen as well as the other cartilage components, several collagen products serve as markers of cartilage degradation in mammal, especially canine articular cartilage injury and loss. Type-II specific collagen breakdown products, e.g., 20-30 amino acid neoepitopes, can be identified in body fluids such as synovial fluid, plasma, serum or urine. The presence of neoepitopes in these body fluids may be used as indicators of OA onset and progression.

Keratan sulfate is a particular GAG which has an epitope, 5D4, whose levels in synovial fluid can be used as a marker of early articular cartilage injury and loss. Conversely, levels of chondroitin sulfate, another particular GAG, expressed as a number of epitopes, is associated with anabolic events in the articular cartilage of mammals in the early stages of cartilage injury and loss. Levels of these epitopes in synovial fluid, particularly 3B3, 7D4 and 846, can be determined by specific monoclonal antibodies which recognize them. The 3B3 epitope is expressed on chondroitin sulfate chains of cartilage during repair and the remodeling of the extracellular matrix, and consequently its levels in synovial fluid correlate inversely with those of the above-mentioned 5D4. The expression of 3B3 in newly synthesized PGs in the superficial and upper middle layer of the articular cartilage mean that 3B3 is associated with early changes in the articular cartilage of mammals in the early stages of cartilage degeneration. Accordingly, the determination of 3B3 levels in the synovial fluid of test mammals and comparison of these levels with control values permits the creation of a diagnostic profile of a mammal that is an appropriate candidate for early pharmacologic treatment.

Further markers of cartilage anabolic activity are the propeptides of type II procollagen (PIIP). Type II is the major collagen of articular cartilage and it is produced by the chondrocytes as procollagen. During the process of collagen fibril formation, the noncollagenous aminopropeptide and carboxypropeptide are cleaved and released into body fluids, where they can be measured as reflection of anabolic activity in the articular cartilage. Levels of carboxy-PIIP will be raised and its synovial fluid levels correlate with radiographic evidence of changes in the cartilage. Accordingly, measurement of carboxy-PIIP levels in synovial fluid and comparison with controls permits identification of mammal candidates for early pharmacologic treatment.

An imbalance in the stromelysin/TIMP ratio in the articular cartilage and joint fluids of mammals in the early stages of articular cartilage degeneration is also useful in identifying such mammals. Altered joint loading following injury causes the production of excess stromelysin, an enzyme produced by chondrocytes and synoviocytes under the influence of IL-1. The concentrations of stromelysin are also higher in fibrillated cartilage than they are in cartilage more distal from the lesion involved. The increased levels of stromelysin may occur for only a fairly short period of time, but where the damage to the joint transcends the tidemark zone of the articular cartilage, and reaches into the subchondral bone, there is a substantial likelihood of subsequent articular cartilage degeneration, usually preceded by a stiffening of the subchondral bone.

Further, in the cruciate-deficient mammal model used in detecting the early stages of articular cartilage degeneration, there is an increased number of cells involved in the synthesis of stromelysin, IL-1α, IL-1β, and three oncogene proteins, c-MYC, c-FOS, and c-JUN. In the synovium these are found mainly in the superficial synovial lining cells, while in the cartilage the cells are the chondrocytes on the superficial and middle layers and the cells in the fibrillated areas of the tibial plateau. Further, stromelysin and IL-1 diffuse into the cartilage matrix of the tibial plateau. Stromelysin, which degrades components of connective tissue including proteoglycans and type IX collagen, is actively synthesized in the synovium of mammals in the early stages of articular cartilage degeneration, and is the primary proteolytic enzyme involved in the cartilage destruction. Increased levels of stromelysin mRNA are detectable in the synovia of such mammals, as are increased levels of collagenase mRNA. Increased levels of both isoforms of IL-1, but especially IL-1β, stimulate the increased synthesis of stromelysin by enhancing synovial fibroblast induction of stromelysin and collagenase gene expression. At the same time, IL-1 does not induce mRNA of tissue inhibitor of metalloprotease (TIMP) and the levels of this inhibitor remain unchanged while the detectable levels of metalloproteases in the synovium are dramatically increased.

The metalloproteases are secreted by chondrocytes as proenzymes which must be activated before degradation of extracellular matrix macromolecules can take place. Activation involves an enzymatic cascade in which serine proteases including the plasminogen activator/plasmin system play a key role.

The integrity of the articular cartilage in a mammal joint depends upon the adequacy of the support which it receives from the bony bed which it covers, i.e., the structural properties of the underlying subchondral bone. Alterations in this bony bed precede degradative changes in the articular cartilage. These alterations include increased stiffening of the subchondral bone, accompanied by loss of shock-absorbing capacity. These subchondral bone changes are caused by inappropriate repair of trabecular microfractures which result, in turn, from excessive loading of the joint. Trabecular thickening of the subchondral bone is part of a bone alteration leading to increased bone mineral density and/or volume in affected joints, which in turn is caused by a bone cell defect in the osteoblasts, resulting in altered phenotypic characteristics in these osteoblast-like cells of the subchondral bone.

These alterations in subchondral bone density are not only evidence of an imbalance in the bone remodeling process, but also are a key ingredient in eventual focal cartilage loss. Bone sclerosis is also due to dysregulation of this bone remodeling process. Further, site-related differences in osteoblast metabolism occur which lead to the production of different cartilage-degrading molecules. These changes in osteoblast metabolites in turn lead to corresponding changes in chondrocyte metabolism, rendering them more susceptible to cytokine-induced activity of the types above-described. This osteoblastic anomaly and differentiated phenotype is characterized by divergent production levels of osteocalcin, alkaline phosphatase, cAMP responsive to hormone challenge, urokinase plasminogen activator (uPA), and insulin-like growth factor 1 (IGF-1).

Further evidence of subchondral bone activity involvement in eventual articular cartilage degeneration is joint space narrowing which may be measured by bone scintigraphy. These changes in subchondral bone activity are accompanied by corresponding changes in specific bone cell metabolites, e.g., osteocalcin. Osteocalcin is a vitamin K-dependent, calcium binding bone protein which is the most abundant noncollagen protein in bone. Increased levels of osteocalcin are a marker of bone turnover in various disease states, including particularly the early stages of articular cartilage degeneration. Body fluid, especially synovial fluid levels of osteocalcin directly correlate to subchondral bone changes as measured by scintigraphy.

In addition to markers of subchondral bone activity as indicators of the early stages of articular cartilage degeneration in mammals, metabolites from cartilage and synovium activity are also useful as markers which indicate the early stages of such cartilage degeneration. For example, detection of increased serum levels of cartilage oligomeric matrix protein serves as a marker of cartilage turnover. Similarly, detection of high levels of hyaluronate in body fluids, especially serum serves as a marker of synovial inflammation. In both cases, the increased body fluid, especially serum levels of these metabolite markers indicate the early stages of articular cartilage degeneration.

The expression "body fluid" as used herein is intended to include all of those accessible body fluids usable as clinical specimens which may contain a compound being tested for in sufficient concentration in said fluid to be within the limits of detection of the test device or assay being used. Body fluids will thus include whole blood, serum, plasma, urine, cerebrospinal fluid, synovial fluid, and interstitial and other extracellular fluids. Accordingly, the afore-described measurements usually are conducted in vitro on a specimen (sample) that has been obtained from the candidate mammal.

BRIEF DESCRIPTION OF THE DRAWINGS

FIG. 1: Table listing macroscopic grading of cartilage changes of femoral condyles and tibial plateaus;

FIG. 2: Table listing histological grading of synovial membrane;

FIG. 3: Table listing cartilage cell score for collagenase-1 (MMP-1) and synovial membrane cell scores for IL-1β in osteoarthritic dogs;

DESCRIPTION OF PREFERRED EMBODIMENTS

Figure 4:
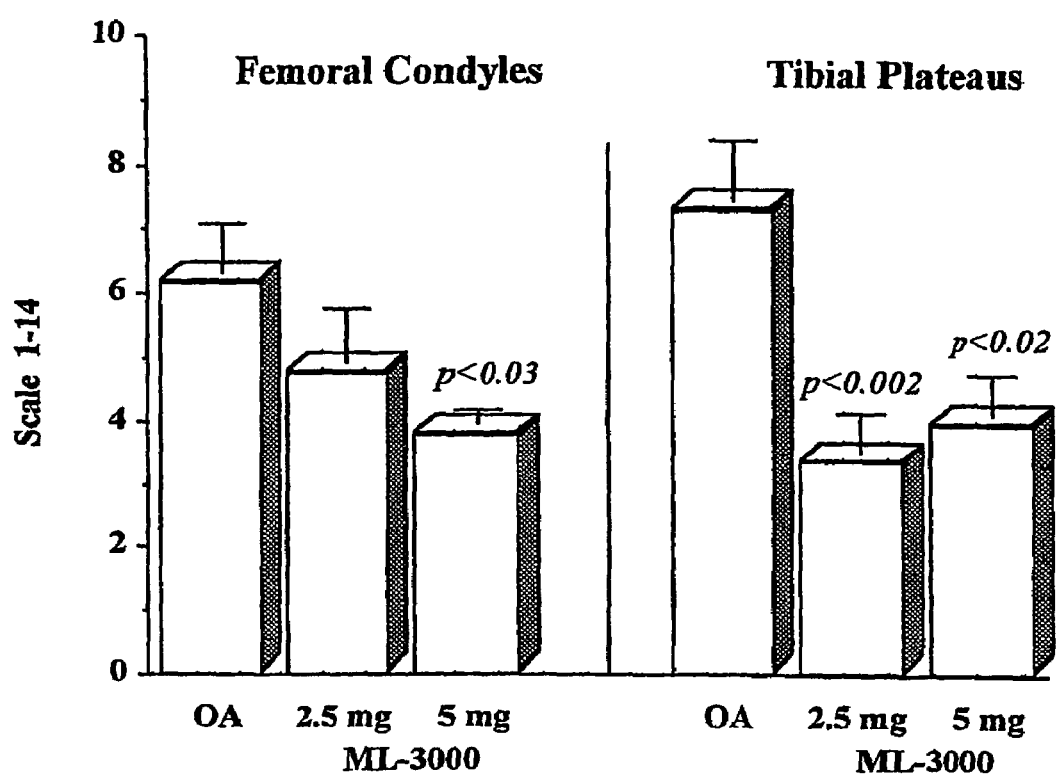
FIG. 4: Histologic grading of dog osteoarthritic cartilage from femoral condyles and tibial plateaus.

In order to further demonstrate the methods and compositions of the present invention, there are presented in the paragraphs which follow specific descriptive examples of typical procedures which may be employed in carrying out said methods. However, said examples are intended to be illustrative only and should not be taken as in any way a limitation of the present invention, for which purpose the present claims are appended hereto.

EXAMPLE 1

The therapeutic effectiveness of ML3000 on the development of lesions in the experimental osteoarthritis (OA) dog model was studied. In particular, the action of ML3000 on the synthesis of collagenase-1 (MMP-1) in cartilage and interleukin-1β (IL-1β) in synovial membrane as well as on alkaline phophatase activity, IGF-1 production, osteocalcin release, $PEG_2$ and uPA activity in or by primary osteoblasts was determined.

Experimental Groups

Twenty-one adult crossbred dogs (2-3 years old), weighing 20-25 kg each, were used in this study. Surgical sectioning of the anterior cruciate ligament (ACL) of the right knee through a stab wound was performed on all dogs as previously described (5,6). Prior to surgery, the animals were anesthetized intravenously with pentobarbital sodium (25 mg/kg) and intubated. Following surgery, the dogs were kept at a housing farm where they were free to exercise in a large pen.

The dogs were randomly separated into 3 treatment groups. Group 1 (n=7 dogs) was made up of dogs that received placebo (encapsulated methylcellulose) treatment (OA dogs); Groups 2 and 3 (n=7 dogs per group) received encapsulated ML3000 twice daily for 8 weeks at total doses of 2.5 and 5 mg/kg, respectively, beginning the day following surgery. The medication was administered 7 days/week throughout the duration of the study. All dogs were killed 8 weeks after surgery.

All dogs in each experimental group completed the study. No clinical signs of drug toxicity, including those related to the gastrointestinal tract, were noted in the group of dogs treated with ML3000. The level of daily activity was similar in all dogs from the 3 experimental groups, and there was no change in the body weight of the dogs during the study period.

Statistical Analysis

Values are expressed as mean±SEM. Statistical analysis was done using the Mann-Whitney U test. P values less than 0.05 were considered significant.

Macroscopic Grading

Immediately after killing, the right knee of each dog was dissected, placed on ice, and the synovial fluid aspirated. Each knee was examined by 2 independent, blinded observers (DVJ, JCF) for gross morphologic changes including the presence of osteophyte formation and cartilage lesions as previously described (5,6). The degree of osteophyte formation was graded by measuring the maximal width (mm) of the spur of each femoral condyle. The cartilage changes on the medial and lateral femoral condyles and tibial plateaus were graded separately under a dissecting microscope (Stereozoom; Bausch & Lomb, Rochester, N.Y.).

The area of the articular surface changes was measured and expressed in $mm^2$. The depth of erosion was graded on a scale of 0-4, as follows: 0=surface appears normal, 1=minimal fibrillation or a slight yellowish discoloration of the surface, 2=erosion extended into superficial or middle layers, 3=erosion extended into deep,layers, and 4=erosion extended to the subchondral bone.

Osteophytes. In placebo-treated OA dogs, osteophytes were present in 93% of the condyles, and their widths measured 4.50±0.66 mm. In dogs treated with 2.5 mg/kg/day and 5 mg/kg/day ML3000, osteophytes were present in 93% and 86% respectively. The width measurements of osteophytes in the two treated groups were marginally smaller compared with the placebo-treated OA group (3.57±0.56 and 3.86±0.66 respectively), and these differences did not reach statistical significance.

Cartilage. In the placebo-treated OA dogs, cartilage lesions of moderately severe grade and size were present on both condyles and plateaus with more severe lesions on the plateaus (FIG. 1). There was a significant reduction in the size of lesions on the condyles and plateaus of both groups treated with ML3000. In the 2.5 mg/kg/day group, the size of lesions on femoral condyles was lower by 39% (P<0.05) and by 45% (P<0.01) on tibial plateaus. In the group that received 5 mg/kg/day, the size of the lesions on femoral condyles was also reduced (61%, P<0.04), while the effect on tibial plateaus was about the same as those found in the 2.5 mg/kg/day group (54%, P<0.01). Both concentrations of ML3000 significantly reduced the grade of lesions on tibial plateaus to about the same extent. Although the lesions on femoral condyles of treated dogs showed a tendency towards a reduction in their grade, it did not reach statistical significance.

Synovial membrane. Synovium from placebo-treated OA dogs was hypertrophic, demonstrated a red and yellowish discoloration and contained a large number of blood vessels. In dogs treated with ML3000, the synovia was thinner, contained fewer blood vessels, and the discoloration was less intense compared with placebo-treated OA dogs.

Histologic Grading

Histologic evaluation was performed on sagittal sections of cartilage from the lesioned areas of each femoral condyle and tibial plateau as described (7,8). Specimens were dissected, fixed in TissuFix #2 (Laboratoires Gilles Chaput, Montréal, Québec, Canada), and embedded in paraffin for histologic evaluation. Serial sections (5 μm) were stained with Safranin O. The severity of the OA lesions was graded on scale of 0-14, by 2 independent observers (DJ, JF), using the histologic/histochemical scale of Mankin et al (12). This scale evaluates the severity of OA lesions based on the loss of staining with Safranin O (scale 0-4), cellular changes (scale 0-3), invasion of the tidemark by blood vessels (scale 0-1), and structural changes (scale 0-6, where 0=normal cartilage structure and 6=erosion of the cartilage down to the subchondral bone). This scoring system was based on the most severe histologic changes within each cartilage section.

Representative specimens of synovial membrane from the gutters of the medial and lateral knee compartments were also dissected from underlying tissue. The specimens were fixed in TissuFix #2, embedded in paraffin, sectioned (5 μm), and stained with hematoxylin and eosin. Two synovial membrane specimens from each compartment were examined, serial selections were made throughout the specimens, and each one scored separately. The highest score from each specimen was recorded. The average was calculated and considered as a unit for the whole knee. The severity of synovitis was graded on a scale of 0-10 (13) by 2 independent observers (DVJ, JCF) adding the scores for 3 histologic criteria: synovial lining cell hyperplasia (scale 0-2), villous hyperplasia (scale 0-3), and degree of cellular infiltration by mononuclear and polymorphonuclear cells (scale 0-5).

Cartilage. Cartilage from placebo-treated OA dogs presented morphologic changes including fibrillation and fissures, hypercellularity and cloning, and a loss of Safranin O staining. Histologic scores for the lesions on the plateaus were slightly more severe than for those on the condyles (FIG. 4). In the ML3000-treated dogs, the lesions on the condyles were less severe compared with the placebo-treated OA dogs, and statistical significance was obtained in the group treated with the highest dosage of the drug (5 mg/kg/day). This reduction in the histologic score was largely due to a decrease in severity of structural changes and loss of Safranin O staining. On tibial plateaus, a statistically significant decrease in the severity of lesions (P<0.002 and P<0.02, respectively) was obtained with both doses of ML3000 (2.5 and 5 mg/kg/day). This results from a decrease in the loss of Safranin O staining and severity of structural changes in addition to a reduction in cell cloning.

Synovial membrane. Synovia from placebo-treated OA dogs was thick, had numerous villi, and showed synovial lining cell hyperplasia. In the ML3000-treated dogs, there was a significant reduction in villous hyperplasia in the 5 mg/kg/day group.

$PGE_2$ Measurement in Synovial Fluid

Synovial fluid taken at the time of sacrifice was centrifuged (14000 g, 15 minutes, 4° C.), and supernatants used for $PGE_2$ determination. The level of $PGE_2$ was determined using a specific enzyme immunoassay (EIA) (Cayman Chemical, Ann Arbor, Mich.).

Figure 5:
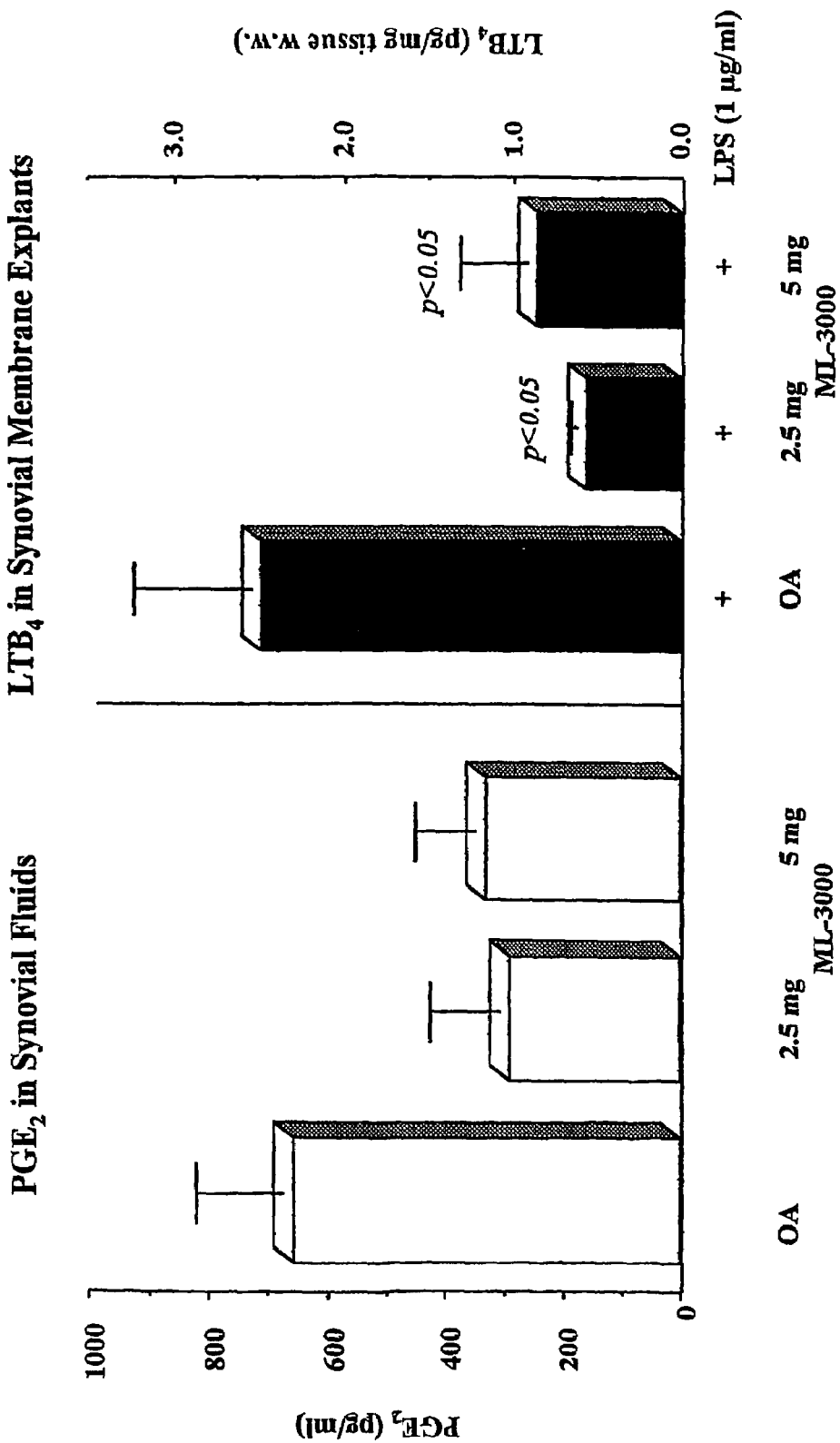
FIG. 5: Levels of $PGE_2$ in the synovial fluids and $LTB_4$ in cultured synovial explants of osteoarthritic dogs.

Synovial fluids from placebo-treated OA dogs contained a high level of $PGE_2$ (652.8±149.9 pg/ml). Treatment with ML3000 at 2.5 and 5 mg/kg/day markedly decreased this level (FIG. 5).

$LTB_4$ Production in Synovial Explant Culture

Representative specimens of synovial membrane from all dogs were aseptically dissected from underlying tissue. The specimens were rinsed several times in Dulbecco's Modified Eagle's Medium (DMEM; Gibco-BRL Life Technologies, Burlington, Ontario, Canada), and 150 mg of tissue incubated (duplicate) for 48 hours at 37° C. in a humidified atmosphere of 5% $CO_2$/95% air in DMEM medium in the presence of 1 μg/ml lipopolysaccharide (LPS; Sigma-Aldrich Canada, Oakville, Ontario, Canada). The $LTB_4$ was extracted from cultured synovium explants as follows: membranes were homogenized in EIA buffer (1 M phosphate, pH 7.4, containing 1% BSA, 4 M NaCl, 10 mM EDTA and 0.1% sodium azide) and centrifuged (30000 g, 20 minutes, 4° C.). Supernatants were collected and the levels of $LTB_4$ determined using EIA (Cayman Chemical).

Cultured synovium from OA dogs treated with 1 μg/ml LPS contained a significant amount of $LTB_4$ (2.48±0.69 pg/mg tissue). Both groups treated with ML3000 demonstrated a statistically significant reduction in $LTB_4$ levels (FIG. 5).

Immunohistochemistry

Cartilage and synovial membrane specimens were processed for immunohistochemical analysis as previously described (7,14). Briefly, specimens were fixed in 4% neutral buffered formalin for 24 hours, then embedded in paraffin. Sections (5 μm) of paraffin-embedded specimens were placed on Superfrost Plus slides (Fisher Scientific, Nepean, Ontario, Canada), deparaffinized in toluene, dehydrated in a graded series of ethanol, and preincubated with chondroitinase ABC (0.25 units/ml) in phosphate buffered saline (PBS; Sigma-Aldrich Canada) for 60 minutes at 37° C. After this, the specimens were washed in PBS, then again in 0.3% hydrogen peroxide/PBS for 30 minutes. Slides were further incubated with a blocking solution (Dako Diagnostics, Mississauga, Ontario, Canada) and 5% skim milk for 60 minutes, blotted and then overlaid with the primary monoclonal antibody against collagenase-1 (100 μg/ml, dilution 1:500, Oncogene Research Products, Cambridge, Mass.) (cartilage) or the primary antibody against human IL-1β (1 μg/ml, dilution 1:50; Biosource International, Camarillo, Calif.) (synovial membrane) for 18 hours at room temperature in a humidified chamber.

Each slide was washed 3 times in PBS (pH 7.4) and stained using the avidin-biotin complex method (Vectastain ABC kit; DAKO Diagnostics Canada). This method entails incubation in the presence of the biotin-conjugated secondary antibody for 30 minutes at room temperature followed by the addition of the avidin-biotin-peroxidase complex for 30 minutes. All incubations were carried out in a humidified chamber and the colour developed with a 3,3'-diaminobenzidine (DAKO Diagnostics Canada) containing hydroxide peroxide. Slides were counterstained with neutral red (cartilage) or hematoxylin/eosin (synovium).

To determine the specificity of staining, 3 control procedures were employed according to the same experimental protocol: 1) use of absorbed immune serum (1 hour, 37° C.) with a 20-fold molar excess of recombinant collagenase-1 or IL-1β; 2) omission of the primary antibody; and 3) substitution of the primary antibody with an autologous preimmune serum. The purified antigens used in our study were human recombinant collagenase-1 (Oncogene Research Products) or human recombinant IL-1β (Genzyme, Cambridge, Mass., USA).

Several sections were made from each block of cartilage, and slides from each specimen, were processed for immunohistochemical analysis. Each section was examined under a light microscope (Leitz Orthoplan; Wild Leitz, St. Laurent, Québec, Canada) and photographed with Kodak Ektachrome 64 ASA film (Kodak, Rochester, N.Y.).

Cartilage (FIG. 3). In placebo-treated dogs, a large number of chondrocytes in the superficial layers of cartilage specimens stained positive for collagenase-1 on both the condyles and plateaus. In the ML3000-treated OA dogs, both condyles and plateaus presented a significant decrease in the chondrocyte cell score for collagenase-1—the effect of which was slightly more pronounced in the group treated with the highest dosage of the drug.

Synovial membrane (FIG. 3). The examination of the synovium samples from placebo-treated OA dogs showed the presence of a large number of lining cells staining strongly positive for IL-1β. In dogs treated with ML3000, there was a dose-dependent and significant decrease in the number of cells showing positive staining for IL-1β.

Morphometric Analysis

Cartilage. Quantification of the different antigens in cartilage was done using a published method (7,14). The presence of the antigen was estimated by determining the number of chondrocytes staining positive in the upper (superficial and upper intermediate layers) zone of cartilage. In this zone, cartilage was divided into 3 microscopic fields (X 40; Leitz Diaplan), and averaged. For each arthritic specimen, it was ensured prior to evaluation that an intact cartilage surface could be detected and used as a marker for validation of morphometric analysis. The total number of chondrocytes and the number of chondrocytes staining positive for the specific antigen were determined. The final results were expressed as the percentage of chondrocytes staining positive for the antigen (cell score) with the maximum score being 100%. Each slide was subjected to double blind evaluation resulting in a variation of <5%. The data obtained from the medial and lateral condyles and tibial plateaus were considered as independent for the purpose of statistical analysis.

Synovial membrane. For synovial membrane analysis, a cell score of the different specimens was determined for each section using our published method (8). Each specimen was divided into 5 microscopic fields (X 40) at the synovial lining level. The percentage of cells staining positive for the specific antigen was evaluated in each field as described above for cartilage. Cell count scores were given separately for the synovial lining cells and mononuclear cell infiltrate with the maximum for each area being 100%.

Osteoblast Analysis

The proximal end of the tibia was removed as below-described, rinsed in a cold physiological saline solution, and placed on ice prior to and throughout dissection. Medial tibial plateaus was extracted to prepare explants and primary bone cell cultures; no marginal cortical bone tissue was included. The overlying cartilage was first removed from the tibial plateaus, and plug explants were dissected out exclusively from the midportion of the medial plateau. The trabecular bone tissue was then dissected away from the subchondral bone plate. All manipulations were performed under a magnifying microscope to ensure complete removal of cartilage and trabecular bone.

The samples were used to prepare primary cell cultures as described in (16), with minor modifications. Bone samples were cut into small pieces (2 mm$^2$) prior to their sequential digestion in the presence of 1 mg/ml type I collagenase (Sigma) in Ham's F-12/Dulbecco's modified Eagle's medium (DMEM; Sigma) without serum, at 37° C. for 20, 20, and 240 minutes. This treatment removed both adherent and remaining bone marrow cells from the cortical bone pieces.

After washing with the same medium, the digested bone pieces were cultured in BGJ medium containing 20% fetal bovine serum (FBS; Wisent, St. Bruno, Quebec, Canada). This medium was replaced every 2 days until cells are observed in the Petri dishes, at which time the culture medium was replaced with fresh medium containing 10% FBS. At confluence, cells were passaged once at a ratio of 25,000 cells/cm$^2$ and are grown in 24-well plates (Falcon, Lincoln Park, N.J.) for 5 days prior to assay. Cells obtained under these culture conditions showed an osteoblast-like cell phenotype, as noted in (16). Conditioning is performed for the last 2 days of culture, in the presence or absence of 50 nM 1,25(OH)$_2$D$_3$ (1,25-dihydroxyvitamin D) for maximal stimulation, in Ham's F-12/DMEM containing 2% charcoal-stripped FBS, which yields maximal stimulation of alkaline phosphatase activity and osteocalcin secretion, as noted (16). The medium was collected at the end of the incubation and frozen at −80° C. prior to assay. Cells were then washed twice with phosphate buffered saline (PBS), pH 7.4, and solubilized in alkaline phosphatase buffer (100 mM glycine, 1 mM MgCl$_2$, 1 mM ZnCl$_2$, 1% Triton X-100; pH 10.5) for 60 minutes with agitation at 4° C.

Osteocalcin Release

Figure 6:
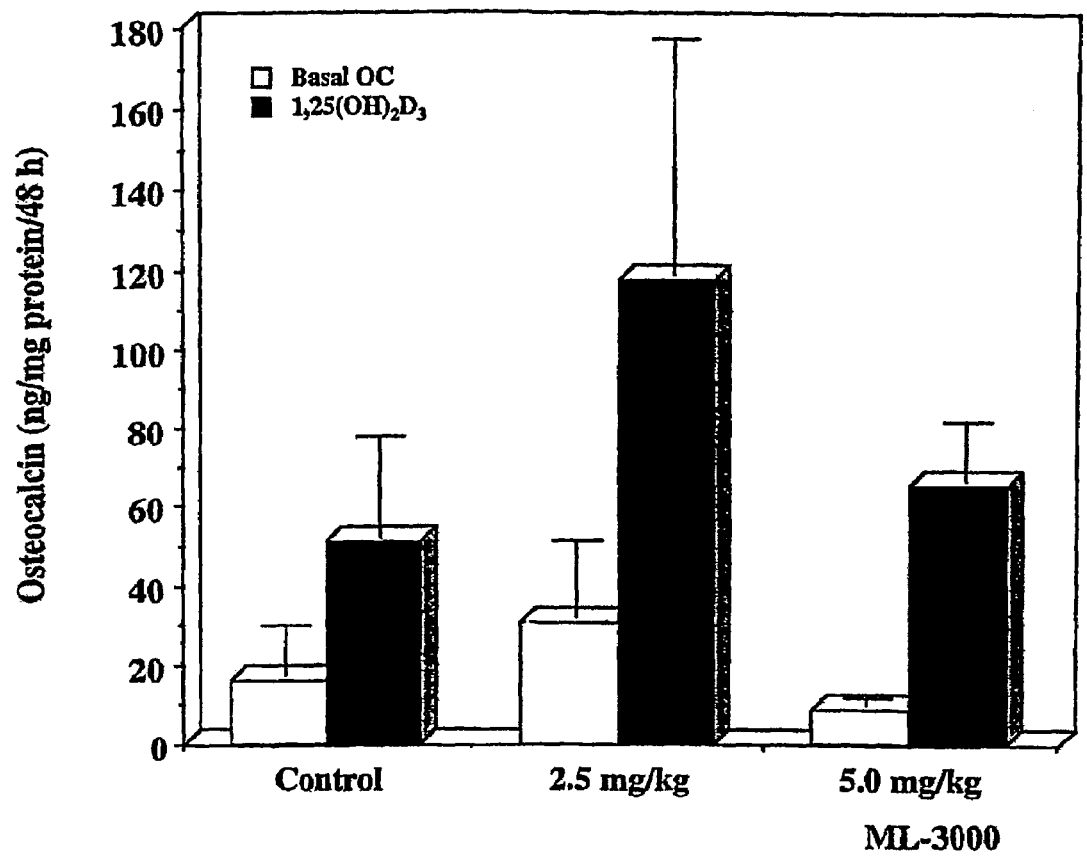
FIG. 6: Osteocalcin release by dog primary osteoblasts.

Osteocalcin release was measured in conditioned Ham's F-12/DMEM (1:1) prepared for the last 2 days of culture of osteoblast-like cells as described in (16), containing 2% charcoal-treated FBS, and in the presence of 50 nM 1,25(OH)$_2$D$_3$ or vehicle (0.1% ethanol). Nascent osteocalcin was determined using a specific enzyme immunoassay (Biomedical Technologies, Stoughton, Mass.). The detection limit of this assay is 0.5 ng/ml, and 2% charcoal-treated FBS contains <0.1 ng/ml osteocalcin. Results are shown in FIG. 6.

Alkaline Phosphatase Activity

Figure 7:
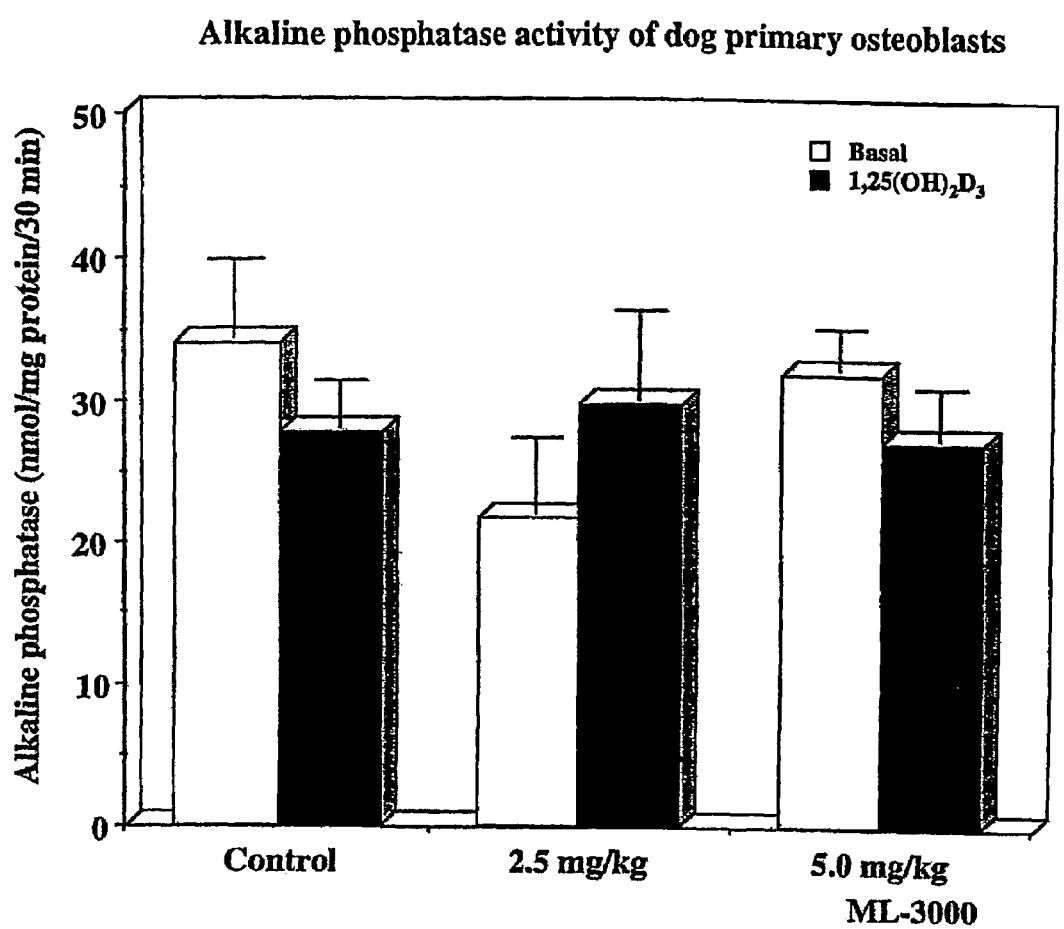
FIG. 7: Alkaline phophatase activity in dog primary osteoblasts.

Cellular alkaline phosphatase activity was determined, on cells used for osteocalcin release, as the release of p-nitrophenol hydrolyzed from p-nitrophenyl phosphate (12.5 mM final concentration) at 37° C. for 30 minutes after solubilizing the cells in alkaline phosphatase buffer as above-described. Alkaline phosphatase was determined immediately on aliquots. Protein determination was performed by the bicinchoninic acid method described in Smith, P. K.; Krohn, R. I.; Hermanson, G. T.; Mallia, A. K.; Gartner, F. H.; Provenzano, M. D.; et al.; "Measurement of Protein Using Bicinchoninic Acid", *Anal Biochem*, 150, 1985, 76-85. Results are shown in FIG. 7.

Evaluation of uPA and IGF-1 in Primary Osteoblasts

Figure 8:
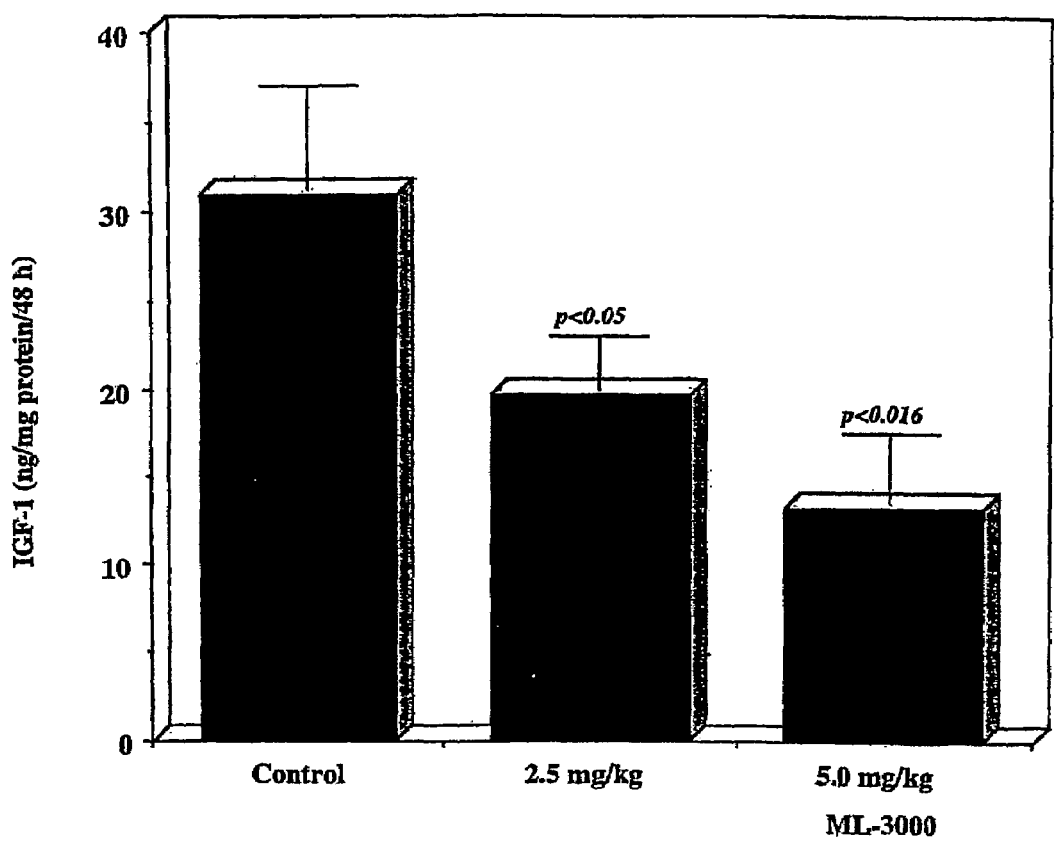
FIG. 8: IGF-1 production by dog primary osteoblasts.
Figure 9:
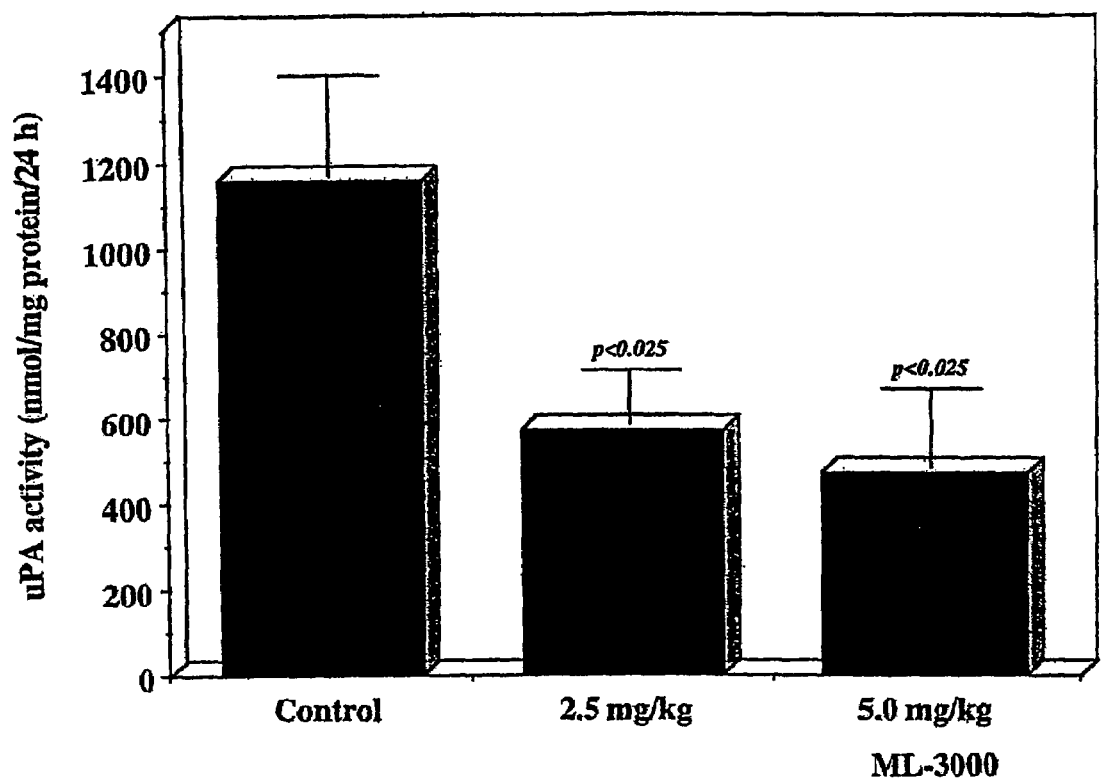
FIG. 9: uPA activity by dog primary osteoblasts.

For evaluation of uPA and IGF-1, the conditioned media from confluent osteoblast-like cells fed with Ham's F-12/DMEM, without PBS, but containing 1% insulin-transferrin-selenium mix (ITS, Sigma) for the last 2 days of culture. First, uPA levels were determined by specific enzyme-linked immunosorbent assay (ELISA; American Diagnostica, Greenwich, Conn.). There was then used the procedure described in Leprince, P.; Rogister, B.; Moonen, G. A.; "Colorimetric Assay for the Simultaneous Measurement of Plasminogen Activators and Plasminogen Ativator Inhibitors in Serum-Free Conditioned Media from Cultured Cells", *Anal Biochem*, 177, 1989, 341-346, to determine the activity of uPA via the hydrolysis of the specific substrate DL-Val-Leu-Arg-p-nitroanilide (Sigma), which releases p-nitroaniline that can be detected at 405 nm. PAI-1 levels are determined by ELISA, using materials available from American Diagnostica (Greewich, Conn.). IGF-1 was determined using a high-sensitivity ELISA (Diagnostic Systems Laboratories, Webster, Tex.) that does not cross-react with insulin. Internal control studies are performed with the media alone containing 1% ITS, and any values obtained should be below the limit of detection. For the conditioned medium of cell culture samples, 3 or 4 supernatants are pooled, lyophilized, and then reconstituted in PBS buffer, pH 7.4. Samples are then treated according to the method described in Mohan, S.; Bautista, C. M.; Herring, S. J.; Linkhart, T. A.; Baylink, D. J.; "Development of Valid Methods to Measure Insulin-Like Growth Factors-I and -II in Bone Cell-Conditioned Medium, *Endocrinology*, 126, 1990, 2534-42. Results are shown in FIGS. 8 and 9.

Evaluation of PGE$_2$ in Primary Osteoblasts

Figure 10:
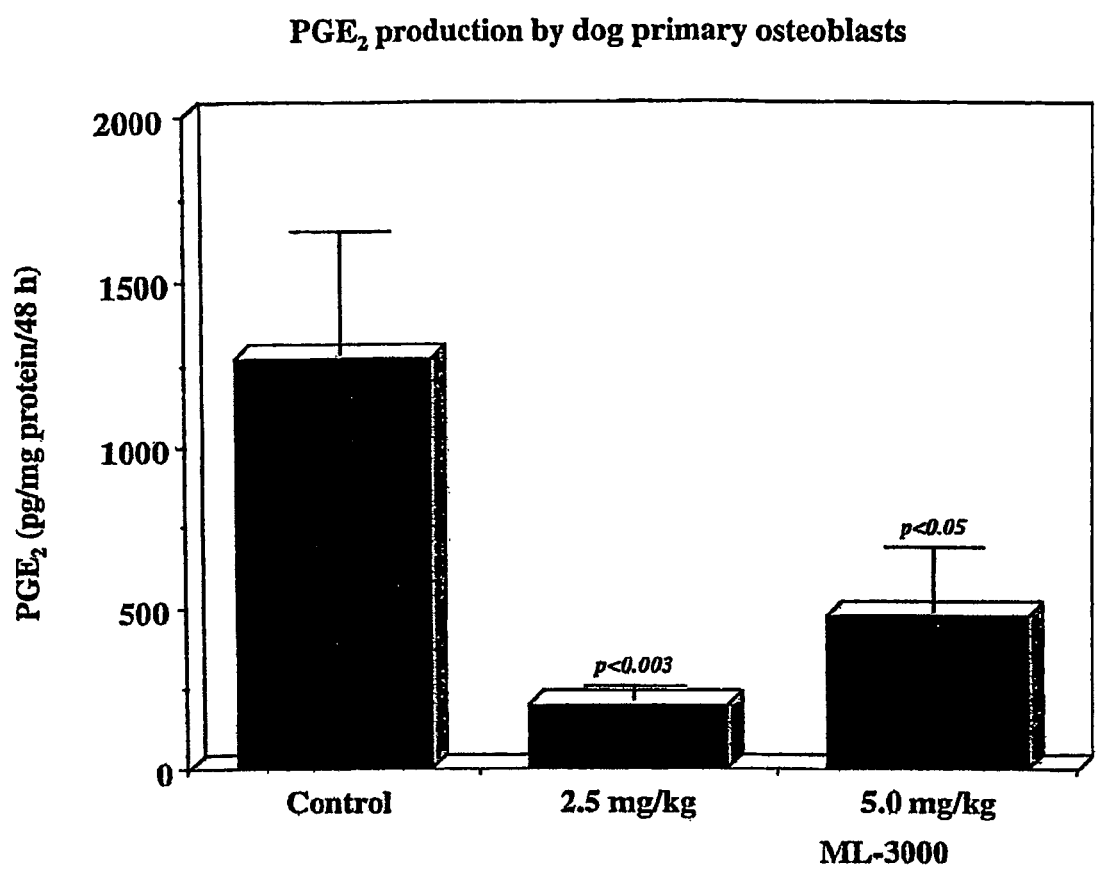
FIG. 10: $PGE_2$ production by dog primary osteoblasts.

PGE2 in primary osteoblasts was determined essentially in the same manner as described above for synovial fluid. Results are shown in FIG. 10.

From the above results it can be concluded that ML3000, a balanced dual inhibitor of COX/5-LO, can significantly reduce the development of early experimental OA at the same time as inhibiting in vivo the production of PGE$_2$ and LTB$_4$. The protective effect of the drug is believed largely related to the marked inhibition of major OA pathophysiological pathways—namely the excess synthesis of IL-1β and collagenase-1. Some of these effects appeared to be linked to the inhibition of the excess production of LTB$_4$.

REFERENCES

1. Pelletier J P, Martel-Pelletier J, Howell D S. Etiopathogenesis of osteoarthritis. In: Koopman W J, editor. Arthritis & Allied Conditions. A Textbook of Rheumatology. 14th ed. Baltimore: Lippincott Williams & Wilkins; 2000. p. 2195-245.
2. Martel-Pelletier J, Di Battista J A, Lajeunesse D. Biochemical factors in joint articular tissue degradation in osteoarthritis. In: Reginster J Y, Pelletier J P, Martel-Pelletier J, Henrotin Y, editors. Osteoarthritis: Clinical and experimental aspects. Berlin: Springer-Verlag; 1999. p. 156-87.
3. Laufer S, Tries S, Augustin J, Dannhardt G. Pharmacological profile of a new pyrrolizine derivative inhibiting the enzymes cyclo-oxygenase and 5-lipoxygenase. Arzneimittelforschung 1994;44:629-36.
4. Laufer S, Tries S, Augustin J, Elsasser R, Albrecht W, Guserle R, et al. Acute and chronic anti-inflammatory properties of [2,2-dimethyl-6-(4-chlorophenyl)-7-phenyl-2,3-dihydro-1H-pyrrolizine-5-yl]-acetic acid. Arzneimittelforschung 1995;45:27-32.
5. Fernandes J C, Martel-Pelletier J, Otterness I G, Lopez-Anaya A, Mineau F, Tardif G, et al. Effects of tenidap on canine experimental osteoarthritis: I. Morphologic and metalloprotease analysis. Arthritis Rheum 1995;38:1290-303.
6. Pelletier J P, Mineau F, Raynauld J P, Woessner J F Jr, Gunja-Smith Z, Martel-Pelletier J. Intraarticular injections with methylprednisolone acetate reduce osteoarthritic lesions in parallel with chondrocyte stromelysin synthesis in experimental osteoarthritis. Arthritis Rheum 1994;37: 414-23.
7. Pelletier J P, Lascau-Coman V, Jovanovic D, Fernandes J C, Manning P, Currie M G, et al. Selective inhibition of inducible nitric oxide synthase in experimental osteoarthritis is associated with reduction in tissue levels of catabolic factors. J Rheumatol 1999;26:2002-14.
8. Fernandes J C, Martel-Pelletier J. Jovanovic D, Tardif G, Di Battista J A, Lascau-Coman V, et al. The effects of tenidap on canine experimental osteoarthritis. II: Study of the expression of collagenase-1 and interleukin-1 beta by in situ hybridization. J Rheumatol 1998;25:951-8.
9. Pelletier J P, Lajeunesse D, Jovanovic D V, Lascau-Coman V, Jolicoeur F C, Hilal G, et al. Carprofen simultaneously reduces progression of morphological changes in cartilage and subchondral bone in experimental dog osteoarthritis. J Rheumatol 2000;27:2893-902.
10. Pelletier J P, Martel-Pelletier J. In vivo protective effects of prophylactic treatment with tiaprofenic acid or intraarticular corticosteroids on osteoarthritic lesions in the experimental dog model. J Rheumatol Suppl 1991;27:127-30.
11. Palmoski M J, Brandt K D. In vivo effect of aspirin on canine osteoarthritic cartilage. Arthritis Rheum 1983;26: 994-1001.
12. Mankin H J, Dorfman H, Lippiello L, Zarins A. Biochemical and metabolic abnormalities in articular cartilage from osteoarthritic human hips. II. Correlation of morphology with biochemical and metabolic data. J Bone Joint Surg Am 1971;53:523-37.
13. Pelletier J P, Martel-Pelletier J, Ghandur-Mnaymneh L, Howell D S, Woessner J F Jr. Role of synovial membrane inflammation in cartilage matrix breakdown in the Pond-Nuki dog model of osteoarthritis. Arthritis Rheum 1985; 28:554-61.
14. Moldovan F, Pelletier J P, Hambor J, Cloutier J M, Martel-Pelletier J. Collagenase-3 (matrix metalloprotease 13) is preferentially localized in the deep layer of human arthritic cartilage in situ: In vitro mimicking effect by transforming growth factor beta. Arthritis Rheum 1997;40:1653-61.
15. Huskisson E C, Berry H, Gishen P, Jubb R W, Whitehead J. Effects of antiinflammatory drugs on the progression of osteoarthritis of the knee. LINK Study Group. Longitudinal Investigation of Nonsteroidal Antiinflammatory Drugs in Knee Osteoarthritis. J Rheumatol 1995;22:1941-6.
16. Lajeunesse, D.; Busque, L.; Ménard, P.; Brunette, M. G.; Bonny, Y.; "Demonstration of an Osteoblast Defect in Two Cases of Human Malignant Osteoporosis: Correction of the Phenotype after Bone Marrow Transplant"; *J. Clin Invest*, 98, 1996, 1835-1842.

The invention claimed is:
1. A method for ameliorating degeneration or destruction in articular cartilage and/or subchondral bone prior to the development of manifest osteoarthritis, comprising administering to a mammal in need thereof a chondroprotective amount of [6-(4-chlorophenyl)-2,2-dimethyl-7-phenyl-2,3-dihydro-9H-pyrrolizine-5-yl]-acetic acid of the formula (Ia):

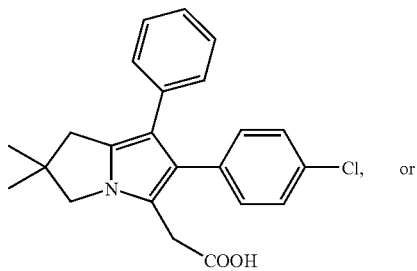

a physiologically acceptable salt or a physiologically hydrolysable ester thereof.
2. The method according to claim 1, which ameliorates degeneration of articular cartilage.
3. The method according to claim 1, which ameliorates destruction of articular cartilage.
4. The method according to claim 1, wherein said mammal is human.
5. The method according to claim 1, wherein said mammal is a cat or dog.
6. The method according to claim 1, wherein said mammal is a horse.
7. The method according to claim 1, which ameliorates injury, damage or loss of articular cartilage.
8. The method according to claim 1, which ameliorates injury, damage or loss of subchondral bone.
9. The method according to claim 1, wherein injury and loss of articular cartilage is asymptomatic.
10. The method according to claim 1, wherein said degeneration or destruction is determined by one or more positive results from a biochemical test performed on body fluids or joint tissue of a mammal with respect to one or more of the following substances:
    (1) increased interleukin-1 beta (IL-β);
    (2) increased tumor necrosis factor alpha (TNFα);
    (3) increased ratio of IL-1β to IL-1 receptor antagonist protein (IL-1 Ra);
    (4) increased expression of p55 TNF receptors (p55 TNF-R);
    (5) increased interleukin-6 (IL-6); increased leukemia inhibitory factor (LIF);
    (6) unchanged or decreased insulin-like growth factor-1 (IGF-1);
    (7) decreased transforming growth factor beta (TGFβ); unchanged or decreased platelet-derived growth factor (PDGF); and
    (8) unchanged or decreased basic fibroblast growth factor (b-FGF).
11. The method according to claim 1, wherein said degeneration or destruction is determined by one or more positive results from a biochemical test performed on body fluids or joint tissue of a mammal with respect to one or more of the following substances:
    (9) increased keratin sulfate;
    (10) increased matrix metalloproteases (MMPs) including stromelysin;
    (11) increased ratio of matrix metalloproteases (MMPs) including stromelysin, to tissue inhibitor of metalloproteases (TIMP);
    (12) increased osteocalcin;
    (13) increased alkaline phosphatase;

(14) increased cAMP responsive to hormone challenge;
(15) increased urokinase plasminogen activator (uPA);
(16) increased cartilage oligomeric matrix protein;
(17) presence of type-II specific collagen neoepitopes and
(18) increased collagenase.

12. The method according to claim 1, wherein said compound of formula (Ia) is administered in an amount of 0.5-10 mg/kg/day.

13. The method according to claim 1, which includes administering in addition to the compound of formula (Ia), the salt or the ester thereof, one or more members selected from the group consisting of polysulfated glycosaminoglycan (PSGAG), glucosamine, chondroitin sulfate (CS), hyaluronic acid (HA), and pentosan polysulfate (PPS).

14. The method according to claim 1, which includes administering in addition to the compound of formula (Ia), the salt or the ester thereof, one or more members selected from the group consisting of doxycycline and minocycline.

15. The method according to claim 1, which includes administering in addition to the compound of formula (Ia), the salt or the ester thereof, one or more antibiotics, antifungal, antiprotozoal, or antiviral agent(s).

16. The method according to claim 1, which includes administering in addition to the compound of formula (Ia), the salt or the ester thereof one or more NSAIDs.

17. The method according to claim 1, which includes administering in addition to the compound of formula (Ia), the salt or the ester thereof, one or more inhibitors of mediators of inflammation.

18. The method according to claim 1, wherein said compound of formula (Ia), its salt or ester, is locally injected, infused, implanted, deposited, inserted, or instilled.

19. The method according to claim 1, wherein said compound of formula (Ia), its salt or ester, is administered in a delayed-release, extended-release, sustained-release, or controlled-release form in combination with a bioerodable polymer.

* * * * *